US012765947B2

(12) United States Patent
Han et al.

(10) Patent No.: US 12,765,947 B2
(45) Date of Patent: Oct. 20, 2026

(54) MAGNETIC RESONANCE GUIDED LASER ABLATION TREATMENT SYSTEM

(71) Applicant: SINOVATION (BEIJING) MEDICAL TECHNOLOGY CO. LTD, Beijing (CN)

(72) Inventors: Meng Han, Beijing (CN); Wenbo Liu, Beijing (CN); Kevin Ai Xin Jue Luo, Beijing (CN); Zhao Wu, Beijing (CN)

(73) Assignee: SINOVATION (BEIJING) MEDICAL TECHNOLOGY CO. LTD, Beijing (CN)

( * ) Notice: Subject to any disclaimer, the term of this patent is extended or adjusted under 35 U.S.C. 154(b) by 543 days.

(21) Appl. No.: 18/270,437

(22) PCT Filed: Dec. 31, 2021

(86) PCT No.: PCT/CN2021/143786
§ 371 (c)(1),
(2) Date: Jun. 29, 2023

(87) PCT Pub. No.: WO2022/143996
PCT Pub. Date: Jul. 7, 2022

(65) Prior Publication Data
US 2024/0099772 A1 Mar. 28, 2024

(30) Foreign Application Priority Data
Dec. 31, 2020 (CN) ......................... 202011640255.6

(51) Int. Cl.
*A61B 34/20* (2016.01)
*A61B 18/22* (2006.01)
(Continued)

(52) U.S. Cl.
CPC .............. *A61B 18/22* (2013.01); *A61B 34/10* (2016.02); *A61B 34/20* (2016.02);
(Continued)

(58) Field of Classification Search
CPC .................... A61B 18/22; A61B 34/20; A61B 2018/00023; A61B 2018/00321;
(Continued)

(56) References Cited

U.S. PATENT DOCUMENTS 6,283,955 B1 * 9/2001 Pacala .................... A61B 18/24 606/7
6,418,337 B1 7/2002 Torchia et al.
(Continued)

FOREIGN PATENT DOCUMENTS

| | | | | |
|---|---|---|---|---|
| CN | 102238921 A | | 11/2011 | |
| CN | 104602638 A | | 5/2015 | |
| CN | 108805991 A | | 11/2018 | |
| CN | 108836477 A | * | 11/2018 | ............. A61B 18/22 |
| CN | 111773567 A | | 10/2020 | |

OTHER PUBLICATIONS

International Search Report of PCT/CN2021/143786.
Written Opinion of PCT/CN2021/143786.

*Primary Examiner* — Benjamin J Klein
*Assistant Examiner* — Alisha J Sircar

(57) ABSTRACT

A magnetic resonance guided laser ablation treatment system, including: an optical fiber cooling assembly (400), accommodating and cooling an ablation optical fiber (5); a laser ablation apparatus (200), including a laser generator and a cooling device; a stereotactic driving system (300), accommodating and controlling the position and angle of rotation of the ablation optical fiber (5); and a workstation (100), configured to control the movement of a stereotactic driving system, and generate and display ablation information of the target region during the workflow of the magnetic resonance guided laser ablation treatment system by using the magnetic resonance temperature imaging technology.

15 Claims, 9 Drawing Sheets

(51) Int. Cl.
*A61B 34/10* (2016.01)
*A61B 18/00* (2006.01)

(52) U.S. Cl.
CPC ............... *A61B 2018/00023* (2013.01); *A61B 2018/00321* (2013.01); *A61B 2018/00595* (2013.01); *A61B 2018/00702* (2013.01); *A61B 2018/00714* (2013.01); *A61B 2034/105* (2016.02); *A61B 2034/107* (2016.02); *A61B 2034/108* (2016.02); *A61B 2034/2051* (2016.02); *A61B 2034/2065* (2016.02)

(58) Field of Classification Search
CPC ........... A61B 2018/00595; A61B 2018/00702; A61B 2018/00714; A61B 2034/105; A61B 2034/107; A61B 2034/108; A61B 2034/2051; A61B 2017/00128; A61B 2018/00208; A61B 2018/00446; A61B 2018/00642; A61B 18/24; A61B 2018/00577; A61B 2018/00744; A61B 2018/00791; A61B 2090/374
See application file for complete search history.

(56) References Cited

U.S. PATENT DOCUMENTS

| | | | |
|---|---|---|---|
| 2002/0193682 | A1 | 12/2002 | Torchia et al. |
| 2019/0247120 | A1 | 8/2019 | Greenwood et al. |

* cited by examiner

MAGNETIC RESONANCE GUIDED LASER ABLATION TREATMENT SYSTEM

CROSS-REFERENCE TO RELATED APPLICATIONS

This application is a national stage application of PCT/CN2021/143786. The present disclosure claims priorities from PCT Application No. PCT/CN2021/143786, filed Dec. 31, 2021, and from the Chinese patent application No. 202011640255.6, filed on Dec. 31, 2020, and entitled "MAGNETIC RESONANCE GUIDED LASER ABLATION TREATMENT SYSTEM", the entire contents of which are incorporated herein by reference.

TECHNICAL FIELD

The present disclosure relates to the technical field of medical devices, in particular to a magnetic resonance guided laser ablation treatment system.

BACKGROUND ART

A laser interstitial thermotherapy is a promising method for treatment of diseases such as focal epilepsy, a malignant tumor and postradiotherapy gangrene of a brain. Laser exerts energy on a disease position and implements ablation for tissue. However, some problems still remain unsolved, first, some manufacturers design a mechanism for controlling movement of the tail end of an optical fiber, but a head-mounted structure for guiding and controlling the optical fiber to enter a skull is complicated and too heavy and needs to be secured and structurally strengthened by using an auxiliary device with a plurality of bone screws, and patients, especially children, hardly accept trauma of implantation of the bone screws and are poor in compliance; second, a range of tissue to be ablated by a laser is limited, so there is a demand for implanting a plurality of optical fibers for ablation, but the existing head-mounted structure occupies too large area, interferes with or severely limits implantation distances of different optical fibers and limits planning of implantation sites, which makes it impossible to perform a solution of too small implantation site distances; third, in order to ablate target ablation tissue which is in an irregular volume, and implement accurate control over an angle of a light-emitting direction and light-emitting time of the optical fiber, namely, accurate control over rotation, especially, in a case that a cooling sleeve is used for cooling, a cooling sleeve assembly may cause non-rigid fixation to the optical fiber passing through it, and consequently, the tail end of the optical fiber is caused to rotate uncontrollably, and laser emission is caused to deviate from a designed expected position; and finally, an ablation assembly rotates in a human body and causes harm to tissue around a path (especially brain tissue).

In order to solve one or more above problems, the present disclosure provides a magnetic resonance guided laser ablation treatment system.

SUMMARY

In view of this, an objective of the present disclosure is to provide a magnetic resonance guided laser ablation treatment system, which can effectively ablate regular tissue and irregular tissue.

In a first aspect, an embodiment of the present disclosure provides a first type of magnetic resonance guided laser ablation treatment system, including:

- an ablation optical fiber;
- a laser ablation apparatus, including a laser generator and a cooling device;
- a stereotactic driving system, accommodating and controlling a position and/or a rotation angle of the ablation optical fiber; and
- a workstation, configured to: control the movement of the stereotactic driving system, and generate and display ablation information of the target region during the workflow of the magnetic resonance guided laser ablation treatment system by using magnetic resonance temperature imaging technology.

Optionally, the ablation optical fiber may emit light laterally.

The stereotactic driving system includes:

- a guide device, a sleeve, a connector and a rotation driving device;
- the near end of the sleeve is connected to the connector, and the far end of the sleeve may extend out from the far end of the guide device; and
- in a use state, the ablation optical fiber is arranged in the sleeve, and the rotation driving device drives the ablation optical fiber to rotate.

Optionally, the rotation driving device includes a first driver; and

- the first driver is connected with the ablation optical fiber, and the first driver drives the ablation optical fiber to rotate about the major axis of the ablation optical fiber.

Optionally, the above stereotactic driving system further includes a controller, and the first driver is connected in communication with the controller;

- in a use state, the controller sends a movement control command to the first driver; and
- the first driver drives the ablation optical fiber to rotate about the major axis of the ablation optical fiber according to the movement control command.

Optionally, the rotation driving device further includes a first angle sensor, and the first angle sensor is connected in communication with the controller; and

- the first angle sensor detects the rotation angle of the ablation optical fiber or a rotation angle of another part the same as the rotation angle of the ablation optical fiber, and sends the detected rotation angle to the controller.

Optionally, the above stereotactic driving system further includes an axial movement driving device; and

- the rotation driving device is in sliding connection with the axial movement driving device.

Optionally, the axial movement driving device is connected in communication with the controller;

- the controller sends an axial translation instruction to the axial movement driving device; and
- the axial movement driving device drives the rotation driving device to perform axial translation according to the axial translation instruction, so as to drive the ablation optical fiber to perform axial translation.

Optionally, the rotation driving device further includes a rotation device base; and

- the first driver is mounted on the rotation device base.

Optionally, the rotation driving device further includes an ablation optical fiber adapter; and in a use state, the first driver drives the ablation optical fiber adapter to rotate, and the far end of the ablation optical fiber adapter is connected with the ablation optical fiber.

Optionally, the guide device includes a hollow guiding part for a elongated structure and a clamping assembly, the far end of the clamping assembly is connected with the near end of the hollow guiding part for the elongated structure, and the clamping assembly is used for fixing the relative positions of the sleeve and the hollow guiding part for the elongated structure after the sleeve extends out of the far end of the hollow guiding part for the elongated structure.

Optionally, the clamping assembly includes an elastic plug, a clamping adapter, a jackscrew and a fastener;

the fastener is in threaded connection with the jackscrew, the far end of the jackscrew is inserted into the clamping adapter and makes contact with the elastic plug, the far end of the fastener may be in threaded connection with the near end of the clamping adapter, the far end of the clamping adapter is connected with the near end of the hollow guiding part for the elongated structure, and the elastic plug is arranged in a cavity of the near end of the hollow guiding part for the elongated structure; and in a use state, the fastener is tightened to the jackscrew and the clamping adapter, the jackscrew tightly compresses the elastic plug, the sleeve penetrates through the jackscrew, the elastic plug and the hollow guiding part for the elongated structure, the far end of the sleeve may extend out of the far end of the hollow guiding part for the elongated structure, and the elastic plug fixes a position of the sleeve.

Optionally, the connector is a hollow shell, and the near end of the sleeve is connected to the hollow shell.

Optionally, the connector includes a sealing plug, an ablation optical fiber connector, and in sequence from near end to far end, a sealing nut, a Luer taper, a water inlet adapter, and a water outlet adapter;

the ablation optical fiber connector is connected with a transmission part of the rotation driving device, and the sealing plug is arranged in the Luer taper, and an internal protrusion of the sealing nut makes contact with the sealing plug; and in a use state, the sealing nut is tightened to the Luer taper, the internal protrusion of the sealing nut tightly compresses the sealing plug, and the ablation optical fiber is arranged within the inside lumen of the ablation optical fiber connector, the sealing nut, the sealing plug and the water inlet adapter to enter the sleeve.

Optionally, the connector further includes a first water pipe and a second water pipe, and the sleeve includes an internal water circulation pipe and an external water circulation pipe;

the internal water circulation pipe is arranged in the external water circulation pipe, a gap exists between the two, the first water pipe penetrates through the water inlet adapter to communicate with the internal water circulation pipe, and the second water pipe penetrates through the water outlet adapter to communicate with the external water circulation pipe; and in a use state, the ablation optical fiber is arranged through the inside lumen of the ablation optical fiber connector, the sealing nut and the sealing plug to enter the internal water circulation pipe.

Optionally, a first strength enhancing structure is arranged between the external water circulation pipe and the internal water circulation pipe, and a second strength enhancing structure is arranged between the internal water circulation pipe and the ablation optical fiber.

Optionally, a rigid structure is arranged on the outside of at least the first portion of the ablation optical fiber, or at least the first portion of the ablation optical fiber has an external surface structure with enhanced strength, wherein the first portion comprises a portion of the ablation optical fiber which begins from the proximal end to the inside of the sealing plug and a portion of the ablation optical fiber which exceeds the far end of the sealing plug, and when the far end of the ablation optical fiber is located at the farthest end of the system, the length of the portion exceeding the far end of the sealing plug is greater than the translation movement range of the ablation optical fiber.

Optionally, the axial movement driving device includes an axial movement driving device base, at least one sliding rail, a lead screw, a sliding block and a second driver; and at least one sliding rail and the lead screw are arranged in parallel and is arranged through the sliding block, the two ends of at least one sliding rail are securely mounted on the axial movement driving device base, the lead screw is connected to the axial movement driving device base, the second driver drives the lead screw to rotate, the second driver is mounted on the axial movement driving device base, and the rotation driving device is mounted on the sliding block.

Optionally, the workstation may be connected in communication with the laser ablation apparatus and the stereotactic driving system, adjust parameters of the laser generator and the cooling device, control the position and the rotation angle of the ablation optical fiber, perform ablation under magnetic resonance detection, and using temperature and ablation information from magnetic resonance images as feedback, perform control over the laser ablation apparatus and the stereotactic driving system.

In a second aspect, an embodiment of the present disclosure provides another type of magnetic resonance guided laser ablation treatment system, including:

an optical fiber cooling assembly, accommodating and cooling an ablation optical fiber;

a laser ablation apparatus, including a laser generator and a cooling device;

a stereotactic driving system, accommodating and controlling a position and/or a rotation angle of the ablation optical fiber; and a workstation, configured to: control the movement of the stereotactic driving system, and generate and display ablation information of the target region during the workflow of the magnetic resonance guided laser ablation treatment system by using magnetic resonance temperature imaging technology.

Further, the workstation is connected with a picture archiving and communication system of a hospital, a digital image is obtained before surgery, a surgery plan is generated according to the digital image, the surgery plan is sent to the laser ablation apparatus, a real-time temperature image of a lesion region is generated by fusion during the surgery by using the magnetic resonance temperature imaging technology, control information is generated according to the real-time temperature image, and the control information is sent to the laser ablation apparatus so as to regulate and control laser power and cooling power of the laser ablation apparatus in real time;

the laser ablation apparatus is connected with the workstation and configured to generate and adjust laser light according to the surgery plan and the control information, and drive and control circulation of a cooling interstitial substance, and the laser ablation apparatus includes a medical switch device, the laser generator, the cooling device, a sensor module, an interaction module and a main control module;

the sensor module is connected with the main control module, and configured to collect working parameter information of a laser thermotherapy device and send the working parameter information to the main control module;

the interaction module is connected with the main control module, and configured to obtain operation instruction information, send the operation instruction information to the main control module and display a working state of the laser thermotherapy device;

the main control module is connected with the workstation, and configured to control the cooling device and the laser generator according to the surgery plan, the working parameter information, the operation instruction information and the control information, where the control information includes first control information and second control information, and the main control module is further configured to monitor a safety running parameter of the laser generator and the cooling device, and make the laser thermotherapy device stop urgently and/or adjust the cooling device in a case that the safety running parameter exceeds a safety threshold;

the laser generator is connected with the main control module and configured to generate and adjust, according to the first control information, first laser light used for ablation and second laser light used for assisting in locating; and the cooling device is connected with the main control module and configured to drive and control circulation of the cooling interstitial substance according to the second control information.

The medical switch device is connected with the main control module and configured to convert an alternating-current power supply to a direct-current power supply.

The cooling device includes a peristaltic pump, the cooling interstitial substance and a cooling interstitial substance conveying pipe and may further include a thermotank.

Optionally, the ablation optical fiber includes an ablation probe capable of emitting light directionally, and the optical fiber cooling assembly includes a cooling liquid conveying pipe, a cooling sleeve, a water circulation adapter assembly and a sealing plug.

The stereotactic driving system includes:

a guiding device, including a cooling sleeve guide part and a guiding device shell;

at least two sensor assemblies, each including an angle sensor;

a rotation driving device, driving the ablation optical fiber to rotate; and a controller, being connected in communication with the sensor assemblies and the rotation driving device, receiving output angle information from the sensor assemblies, controlling the movement of the rotation driving device and further receiving control information; where in a use state, the far end of the ablation optical fiber is arranged within the inside lumen of the optical fiber cooling assembly, the angle sensors are securely connected to a device or a structure which does not rotate together with the ablation optical fiber, and the stereotactic driving system may make rotation angles of the ablation optical fiber at different sensors remain the same or basically the same.

In some embodiments, in the magnetic resonance guided laser ablation treatment system in the present disclosure, each sensor assembly further includes a rotation locating device, so that the ablation optical fiber may move along the major axis while the rotation angle is measured, in a use state, the rotation locating device clamps the ablation optical fiber according to a preset pressure, the ablation optical fiber drives the rotation locating device to rotate, and the angle sensors detect the rotation angle of the rotation locating device and send the rotation angle to the controller.

Further, the stereotactic driving system further includes a sleeve, and the sleeve ensures that the length between the first sensor assembly and the second sensor assembly remains secure, and allows the ablation optical fiber to rotate around a major axis and move along the major axis in the sleeve.

Optionally, the stereotactic driving system further includes an axial movement driving device, the rotation driving device may move relative to the axial movement driving device, the controller sends control information to the axial movement driving device, and thus the ablation optical fiber moves along the major axis; and further, the axial movement driving device is connected with the second sensor assembly.

Optionally, in the stereotactic driving system, the guiding device shell includes a bone screw cap, a guiding device shell body and a guiding device shell rear cover; the near end of the cooling sleeve guide part is in threaded connection with the far end of the bone screw cap, the near end of the bone screw cap is connected with the far end of the guiding device shell body, the guiding device shell rear cover covers the near end of the guiding device shell body, the guiding device shell rear cover is connected with the far end of the sleeve, and the optical fiber cooling assembly is arranged in the guiding device shell body; and in a use state, the ablation optical fiber arranged through the guiding device shell rear cover, the guiding device shell body, the bone screw cap and the cooling sleeve guide part.

Further, the guiding device shell body includes a guiding device shell body fixed portion and a guiding device shell body sliding portion, the near end of the bone screw cap is connected with the far end of the guiding device shell body fixed portion, the near end of the guiding device shell body fixed portion is connected with the far end of the guiding device shell body sliding portion, and the guiding device rear cover covers the near end of the guiding device shell body sliding portion.

In some other embodiments of the present disclosure, the stereotactic driving system of the magnetic resonance guided laser ablation treatment system includes: the guiding device, a sleeve, an ancillary part, the rotation driving device and an axial movement driving device;

the guiding device includes the cooling sleeve guide part and the guiding device shell, the guiding device shell includes a bone screw cap, a guiding device shell body and a guiding device shell rear cover, the guiding device shell body includes a guiding device shell body fixed portion and a guiding device shell body sliding portion, the near end of the bone screw cap is connected with a far end of the guiding device shell body fixed portion, a near end of the guiding device shell body fixed portion is connected with the far end of the guiding device shell body sliding portion, the guiding device rear cover covers the near end of the guiding device shell body sliding portion, a graduated scale is arranged on the guiding device shell body fixed portion and/or the guiding device shell body sliding portion, the guiding device shell body fixed portion and the guiding device shell body sliding portion may move relative to each other, the graduated scale displays a distance of a relative movement, the first sensor assembly is arranged in the guiding device, and the angle sensor of the first sensor assembly is connected with the guiding device shell body;

the second sensor assembly is arranged in the ancillary part, the angle sensor of the second sensor assembly is connected with a shell of the ancillary part, the ancillary part is connected with the axial movement driving device, and the relative positions of the ancillary part and the axial movement driving device are unchanged;

the far end of the sleeve is connected with the guiding device rear cover, the near end of the sleeve is connected with the ancillary part, and thus a length between the guiding device rear cover and the ancillary part is unchanged;

the rotation driving device is in sliding connection with the axial movement driving device; and in a use state, the optical fiber cooling assembly is arranged within the guiding device shell body.

In another aspect of the present disclosure, in the magnetic resonance guided laser ablation treatment system in the present disclosure, a host or a controller may be loaded with a program of a method for accurately adjusting the rotation angle of the ablation optical fiber.

One method for accurately adjusting the rotation angle of the ablation optical fiber includes the following steps:

the controller causes the ablation optical fiber to rotate in one direction through the rotation driving device, when rotation of the ablation optical fiber measured by the first sensor assembly reaches a preset angle, the controller receives and records rotation of the ablation optical fiber measured by the second sensor assembly at the moment, meanwhile, the rotation driving device is controlled to stop rotating and rotate reversely so that the ablation optical fiber nearby the second sensor assembly rotates reversely for an angle, and the angle is an absolute value of a difference between a second angle and a first angle.

Another method for accurately adjusting the rotation angle of the ablation optical fiber includes the following steps:

the controller causes the ablation optical fiber to rotate in one direction through the rotation driving device, when the first sensor assembly measures that the ablation optical fiber starts rotating, a rotation angle measured by the second sensor assembly at the moment is recorded as a basic rotation angle, and when rotation of the ablation optical fiber measured by the first sensor assembly reaches a preset angle, the rotation driving device is controlled to stop rotating and rotate reversely so that the ablation optical fiber nearby the second sensor assembly rotates reversely for the basic rotation angle.

It may be understood that ablation may be divided into a plurality of steps, that is, rotation may need to be performed many times and stop at different positions for different time, ablation progress is monitored through magnetic resonance temperature imaging, then rotation continues, and the above method may be executed many times continuously or discontinuously.

The magnetic resonance guided laser ablation treatment system in the present disclosure generates a real-time temperature image of a lesion region through fusion during surgery by using the magnetic resonance temperature imaging technology, laser power and cooling power are regulated and controlled in real time through a temperature value of a lesion and surrounding sound tissue, effective ablation for regular and irregular lesions is implemented, ablation estimation is performed during surgery, an ablation boundary is adjusted in real time, and a purpose of conformal ablation is achieved.

The magnetic resonance guided laser ablation treatment system in the present disclosure may generate a surgery plan. The surgery plan includes information corresponding to a laser, where the information includes but is not limited to: a planned ablation volume, laser power, light-emitting time, a light-emitting mode, a cooling liquid flowing rate and an optical fiber catheter inserting path plan;

real-time control, specifically, a temperature is calculated based on a magnetic resonance image, a temperature image is calibrated by using a temperature measurement structure, an ablation optical fiber assembly in a working state and working parameters of a treatment light source module and the cooling device are regulated and controlled in real time, and ablation monitoring is performed in real time; and comparative analysis, specifically, information in a surgery plan corresponding to each laser device is compared with information of the laser device after surgery, ablation result information is generated according to a comparison result and displayed on a man-machine interaction module, where a comparison content includes the following: a planned ablation area or volume, and an actual ablation area or volume after surgery; and the ablation result information at least includes but is not limited to: an ablation area percentage, an ablation volume percentage and a before-and-after-ablation comparison diagram.

In a first aspect, innovation points of the embodiment of the present disclosure include:

1, the rotation driving device drives the ablation optical fiber to rotate so as to achieve control over rotation of the ablation optical fiber, an implantation direction of the ablation optical fiber may be guided through the guide device, orientation control over the ablation optical fiber may be achieved without additionally mounting a supporting structure at a skull, suffering of a patient is relieved, and mounting is simple and convenient.

2, By means of arranging the first angle sensor, a rotation angle of a driving shaft or the rotation angle of the ablation optical fiber may be detected and fed back to the controller; and when the rotation driving device includes the first angle sensor, the rotation angle of the ablation optical fiber with a rigid structure or an external surface structure with enhanced strength may be detected and sent to the controller, and thus rotation control over the ablation optical fiber is achieved.

3, By means of arranging the controller, the controller may control the axial movement driving device to drive the rotation driving device to perform axial translation, so that the ablation optical fiber moves with movement of the rotation driving device, and control over axial translation of the ablation optical fiber is achieved.

4, By means of arranging the hollow guiding part for the elongated structure and the clamping assembly, the relative positions of the sleeve and the hollow guiding part for the elongated structure may be secured; by inserting the far end of the jackscrew into the clamping adapter to make contact with the elastic plug, when the fastener is tightened to the jackscrew and the clamping adapter, the jackscrew may tightly compress the elastic plug, so the elastic plug squeezes the sleeve inside, and thus a purpose of fixing the sleeve is achieved.

5, By means of arranging the sealing plug, making the connector include the first water pipe and the second water pipe and making the sleeve include the internal water circulation pipe and the external water circulation pipe, cooling sealing for the ablation optical fiber is implemented.

6, By means of making at least the first portion of the ablation optical fiber have a rigid structure or an external surface structure with enhanced strength, a strength of the ablation optical fiber is enhanced, and by means of making the first portion include the portion at the near end of the ablation optical fiber that is arranged inside of the sealing plug and a portion exceeding the far end of the sealing plug, and making the length of the portion exceeding the far end of the sealing plug greater than the translation movement range of the ablation optical fiber when the far end of the ablation optical fiber is located at the farthest end of the system, it is guaranteed that the ablation optical fiber located in the sealing plug still has the rigid structure or the external surface structure with enhanced strength even after the ablation optical fiber moves, and an influence of friction between the sealing plug and the ablation optical fiber to rotation of the ablation optical fiber is eliminated.

7, By means of arranging the first strength enhancing structure and the second strength enhancing structure, a strength and puncture capacity of the sleeve are improved, and a situation that deformation is caused by squeezing of an external force and circulation of a cooling fluid is blocked is prevented.

In a second aspect, the embodiment of the present disclosure at least has the following advantages:

1, the guiding device is simple in structure, light in mass and high in reliability, a weight of the guiding device may be supported only through the cooling sleeve guide part (for example, a hollow bone screw) without mounting another auxiliary structure, the number of bone screws to be mounted is reduced, suffering of the patient is relieved, and compliance is improved;

2, in the prior art, a head-mounted structure is too large in occupying area, interferes with or severely limits implantation distances of different optical fibers, and limits planning of implantation sites, which makes it impossible to perform a solution of too small implantation site distances, and in the present disclosure, another structure assisting in the guiding device is avoided, the cooling sleeve guide part may be quite close, and more options are provided for large-range tissue ablation by densely implanting ablation optical fibers;

3, the cooling sleeve does not move relative to brain tissue after being implanted, only the ablation optical fiber therein rotates, and harm to the brain tissue caused by adjusting rotation of the ablation optical fiber is not increased; and 4, under the condition of cooling the ablation optical fiber by using the cooling interstitial substance, the sealing plug at the tail end may cause the ablation optical fiber to continue rotating when rotating to a preset angle, an orientation error is caused, surgery expectation and planning are affected greatly, and accurate ablation cannot be implemented.

In order to make the above objectives, features and advantages of the present disclosure clearer and easier to understand, exemplary embodiments are listed below and described in detail with reference to accompanying drawings.

BRIEF DESCRIPTION OF DRAWINGS

In order to more clearly describe specific implementations of the present disclosure or technical solutions in the prior art, the specific implementations or the accompanying drawings needed in the description in the prior art will be briefly introduced below. Apparently, the accompanying drawings in the following description are some implementations of the present disclosure. Those ordinarily skilled in the art may also obtain other accompanying drawings according to these accompanying drawings without making creative efforts.

In FIG. 1 to FIG. 18, 100 workstation, 200 laser ablation apparatus, 300 stereotactic driving system, 400 optical fiber cooling assembly or ablation optical fiber, 1 guide device, 11 hollow guiding part for elongated structure, 12 clamping assembly, 121 elastic plug, 122 clamping adapter, 123 jackscrew, 124 fastener, 2 sleeve, 21 internal water circulation pipe, 22 external water circulation pipe, 23 first strength enhancing structure, 24 second strength enhancing structure, 3 connector, 31 sealing plug, 32 ablation optical fiber connector, 33 sealing nut, 34 Luer taper, 35 water inlet adapter, 36 water outlet adapter, 37 first water pipe, 38 second water pipe, 4 rotation driving device, 41 first driver, 42 rotation device base, 43 ablation optical fiber adapter, 5 ablation optical fiber, 6 axial movement driving device, 61 axial movement driving device base, 62 sliding rail, 63 lead screw, 64 sliding block, 65 second driver, 66 driven wheel, 67 driving wheel, 7 ancillary part connecting piece, 8 guiding device, 81 hollow guide part for elongated structure, 82 second bone screw cap, 83 transmission sleeve mounting base, 84 guiding device shell body fixed portion, 85 guiding device shell body sliding portion, 86 graduated scale, 87 bone screw adapter bolt, 871 bolt protrusion, 88 second angle sensor, 89 second rotation locating device, 9 transmission sleeve, 51 main body, 511 protrusion, 52 adjustable jacking press, 53 bearing, 54 first shaft, 55 second shaft, 56 first hole, 10 ancillary part, 101 ancillary part shell, 1011 ancillary part upper shell, 1012 ancillary part lower shell, 10121 extending portion, 10122 lower connection portion, 102 ancillary part transmission sleeve mounting base, 103 third angle sensor, 104 third rotation locating device, 44 jumper wire optical fiber connector, 45 jumper wire optical fiber sleeve, 501 ablation optical fiber plug, 50 clamping hole, 60 cooling sleeve, 70 cooling circulation assembly, and 90 cooling circulation assembly cap.

DETAILED DESCRIPTION

In order to make objectives, technical solutions and advantages of the embodiments of the present disclosure clearer, the technical solutions in the present disclosure are clearly and completely described in the following with reference to the accompanying drawings. Apparently, the described embodiments are merely some rather than all of the embodiments of the present disclosure. All other embodiments obtained by those ordinarily skilled in the art based on the embodiments of the present disclosure without making creative efforts fall within the protection scope of the present disclosure.

In the present disclosure, the near end mentioned represents the end of a structure away from an ablation part in an axial direction of ablation optical fiber; and on the contrary, the far end mentioned represents the end of the structure away from the target region in the axial direction of the ablation optical fiber.

Figure 1:
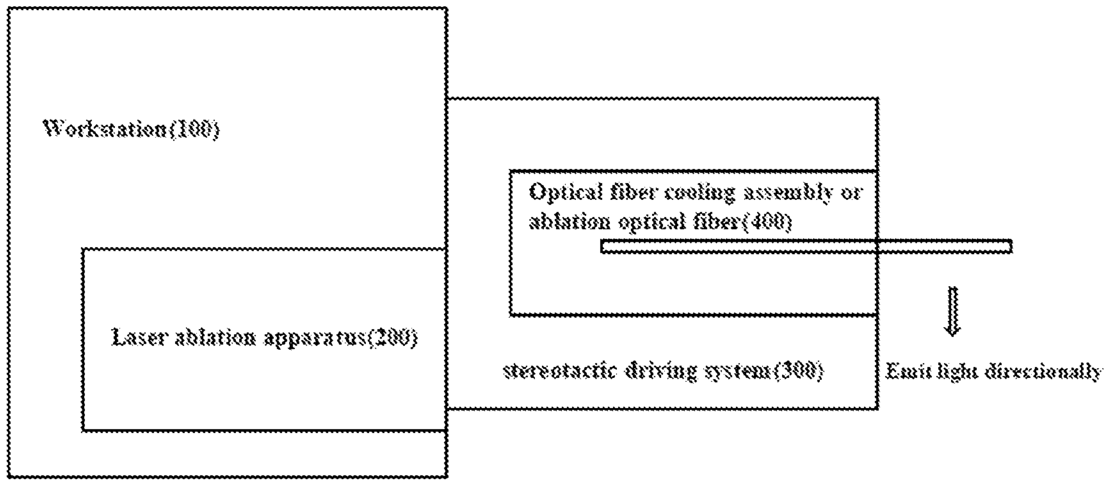
FIG. 1 is schematic diagram of a magnetic resonance guided laser ablation treatment system provided by an embodiment of the present disclosure.

A magnetic resonance guided laser ablation treatment system in the present disclosure, referring to FIG. 1, includes a workstation 100, a laser ablation apparatus 200, a stereotactic driving system 300 and an optical fiber cooling assembly 400 (or an ablation optical fiber 400). A position relationship is not an actual physical structure relationship and is merely schematic. The laser ablation apparatus 200 is connected in communication with the workstation 100, and may be located therein or may exist independently. The laser ablation apparatus 200 and the stereotactic driving system 300 are connected in communication with the workstation 100, which are not necessarily in direct connection structurally and do not limit a structure relationship.

The workstation 100 is arranged to be capable of receiving medical image information (such as CT and MRI), establish a three-dimensional model according to one or more types of medical image information, extract image point cloud based on the three-dimensional model, control the laser ablation apparatus 200 and the stereotactic driving system 300, and calculate and display an ablation progress, and includes an ablation estimation module, and an ablation module is loaded with a program capable of executing an ablation estimation method.

The workstation may generate a surgery plan. The surgery plan includes information corresponding to a laser, where the information includes but is not limited to: a planned ablation volume, laser power, light-emitting time, a light-emitting mode, a cooling liquid flowing rate and an optical fiber catheter inserting path plan;

- real-time control, specifically, a temperature is calculated based on a magnetic resonance image, a temperature image is calibrated by using a temperature measurement structure, an ablation optical fiber assembly in a working state and working parameters of a treatment light source module and a cooling device are regulated and controlled in real time, and ablation monitoring is performed in real time; and
- comparative analysis, specifically, information in a surgery plan corresponding to each laser device is compared with information of the laser device after surgery, ablation result information is generated according to a comparison result and displayed on a man-machine interaction module, where a comparison content includes the following: a planned ablation area or volume, and an actual ablation area or volume after surgery; and the ablation result information at least includes but is not limited to: an ablation area percentage, an ablation volume percentage and a before-and-after-ablation comparison diagram.

The laser ablation apparatus 200 is connected in communication with the workstation 100, may be integrated with or split from the workstation without a requirement for an actual space position, includes a laser generator and a cooling device and may control the laser generator and the cooling device independently or control them by receiving information of the workstation and adjust working power of the laser generator and a cooling interstitial substance flow rate of the cooling device. Optionally, the laser ablation apparatus 200 further includes a sensor module, an interaction module and a main control module. The sensor module is configured to receive information of the tail end of an optical fiber, for example, a temperature sensor arranged at the tail end of the optical fiber and a temperature sensor arranged in a cooling sleeve to monitor laser output power and a cooling condition; and the interaction module is configured to communicate with the workstation, and the main control module sends a command to the laser generator and the cooling device. Six portions included in the laser ablation apparatus 200 are specifically as follows:

(1) a medical switch device, configured to convert an alternating-current power supply of 110 V to 220 V to a direct-current power supply used by each module.

(2) The laser generator, configured to generate laser light used for ablation and laser light used for assisting in locating. A laser light type may be gas, solid, semi-conductor or an optical fiber laser generator. A laser light category may be an infrared ray, an ultraviolet ray or visible light. Ablation mainly applies a wave band of nearby 980 nm and 1064 nm, power is adjustable, maximum power is not greater than 30 W, continuous laser is applied and may be modulated into a pulse laser, a pulse width may be 10 ms to 100000 ms, and a pulse frequency may be 0.01 Hz to 100 Hz. A wave band of the laser light for assisting in locating is mainly nearby 640 nm, power is not greater than 2 W, and continuous laser is applied.

(3) The cooling device, configured to drive and control circulation of a cooling interstitial substance, so as to implement cooling for a laser ablation probe and cooling for probe surrounding tissue.

The cooling device is mainly composed of a thermotank, a peristaltic pump, the cooling interstitial substance and a cooling interstitial substance conveying pipe. A pipe wall pressure sensor is mounted on an inlet and outlet loop portion of a cooling pipe; and a temperature sensor is mounted on a connection portion of the cooling pipe and a thermotank inlet and outlet. The thermotank is configured to make a temperature of the cooling interstitial substance in the cooling pipe remain in a set temperature, and a set range may be 5 to 30 degrees centigrade, and may be generally set as an indoor temperature. The peristaltic pump is configured to provide a circulation force of the cooling interstitial substance and may provide an interstitial substance circulation speed of 0-60 ml/min. The cooling interstitial substance may be normal saline or another light-transmitting liquid. The cooling pipe may be made of a medical rubber material, such as polycarbonate, polyurethane, polyethylene, polypropylene, silicone resin, nylon, PVC, PET, PTFE, ABS, PES, PEEK, FEP and the like.

(4) The sensor module, configured to collect necessary working parameter information in the apparatus. A pipe wall pressure of the inlet and outlet loop portion of the cooling pipe is collected, and whether a leakage exists in a cooling loop may be judged; a temperature of the cooling interstitial substance in the cooling pipe at an inlet and outlet of the thermotank is collected, and whether temperature setting of the thermotank is reasonable may be judged; and a temperature nearby a laser chip of the laser generator is collected, and a working state of the laser generator is judged. Temperature measurement may adopt a thermocouple, a Pt resistor and the like; and pressure measurement adopts a ceramic or thin film pressure sensor.

Data collected by the sensor module are transferred to the main control module through a data interface.

(5) Interaction module: the interaction module is an input and output module of the laser ablation apparatus, is composed of a button and a display screen, is electrically connected with the main control module, obtains operation instruction information of a user side and sends the operation instruction information to the main control module. The interaction module is configured to display and output a working state of the laser ablation apparatus, a rotation speed of the peristaltic pump, laser power, a pulse frequency, a sensor parameter and the like. Meanwhile, the interaction module may input a parameter setting instruction and a switch state instruction.

(6) Main control module:

the main control module is a data collection, issuing, storage and calculation module of the laser ablation apparatus and is electrically connected with the interaction module, the sensor module, the cooling device, the laser generator and the medical switch device. Storage, display and transmission of various data during surgery are completed. The laser generator and the cooling device are controlled to run according to an input parameter, and the laser light, a running state of the cooling device and the sensor parameter are transferred to the workstation and the interaction module. Meanwhile, the main control module may set and monitor the laser light and a safety running parameter of the cooling device, and when an apparatus running parameter exceeds a set safety threshold, the main control module quickly controls the apparatus to stop urgently.

Embodiment 1

A first type of magnetic resonance guided laser ablation treatment system in the present disclosure includes: a workstation 100, a laser ablation apparatus 200, a stereotactic assembly 300 and an ablation optical fiber 400. A cooling assembly is included in the orientation assembly 300, and a cooling device is arranged in the laser ablation apparatus 200.

A structure of a first type of stereotactic driving system 300 of this type of magnetic resonance guided laser ablation treatment system is described in detail below with reference to the accompanying drawings.

Figure 2:
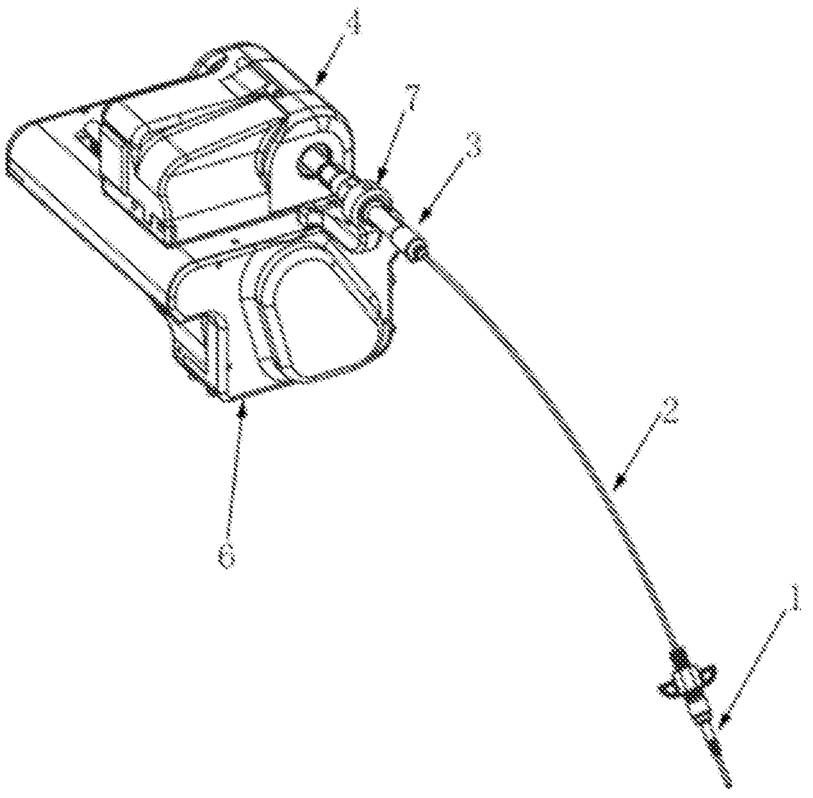
FIG. 2 is a schematic diagram of an assembled structure of a first type of stereotactic driving system provided by an embodiment of the present disclosure.
Figure 3:
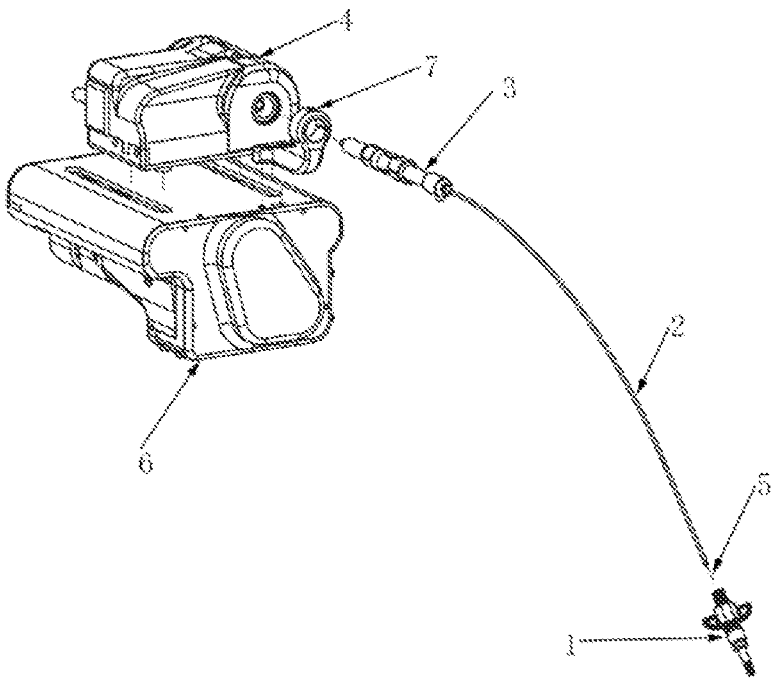
FIG. 3 is a schematic structural explosive view of a first type of stereotactic driving system provided by an embodiment of the present disclosure.

FIG. 2 is a schematic diagram of an assembled structure of a first type of stereotactic driving system provided by an embodiment of the present disclosure. FIG. 3 is a schematic structural explosive view of a first type of stereotactic driving system provided by an embodiment of the present disclosure. Referring to FIG. 2 and FIG. 3, the first type of stereotactic driving system provided by the embodiment of the present disclosure includes: a guide device 1, a sleeve 2, a connector 3 and a rotation driving device 4.

The near end of the sleeve 2 is connected to the connector 3, and the far end of the sleeve 2 may extend out from the far end of the guide device 1. The far end of the sleeve 2 may be the blind end.

In a use state, the ablation optical fiber 5 is arranged in the sleeve 2, and the rotation driving device 4 drives the ablation optical fiber 5 to rotate.

The connector 3 may be secured to any structure as long as the near end of the connector 3 is opposite to the far end of the rotation driving device 4 after fixing, so that the rotation driving device 4 may drive the ablation optical fiber 5 to rotate, and the ablation optical fiber 5 may, in the connector 3, rotate around the major axis of the ablation optical fiber and/or move in an axial direction of the ablation optical fiber. For example, the connector 3 is secured to a special support or may be connected with the rotation driving device 4, or the connector 3 may be connected with an axial movement driving device 6 through a connecting piece 7.

To sum up, the stereotactic driving system provided by the embodiment of the present disclosure includes the guide device 1, the sleeve 2, the connector 3 and the rotation driving device 4, the near end of the sleeve 2 is connected to the connector 3, the far end of the sleeve 2 may extend out from the far end of the guide device 1, and in the use state, the ablation optical fiber 5 is arranged in the sleeve 2, and the rotation driving device 4 drives the ablation optical fiber 5 to rotate. In the embodiment of the present disclosure, the rotation driving device drives the ablation optical fiber to rotate so as to achieve control over rotation of the ablation optical fiber, an implantation direction of the ablation optical fiber may be guided through the guide device, orientation control over the ablation optical fiber may be achieved without additionally mounting a supporting structure at a skull, suffering of a patient is relieved, and mounting is simple and convenient.

Various parts of the stereotactic driving system are introduced in detail below.

Figure 4:
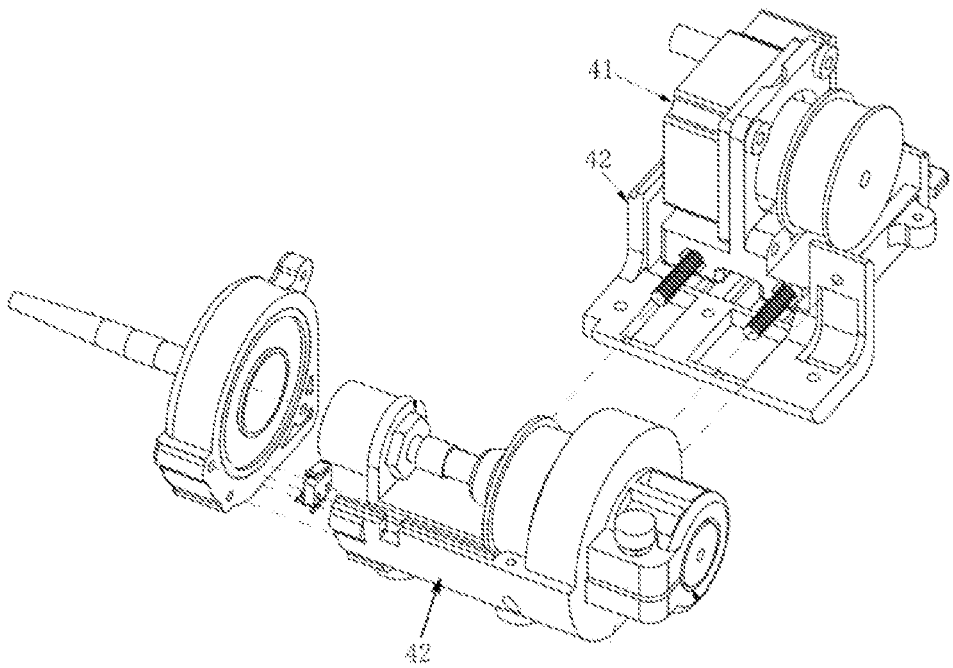
FIG. 4 is a schematic structural diagram of a rotation driving device.

FIG. 4 is a schematic structural diagram of a rotation driving device 4. Referring to FIG. 4, the rotation driving device 4 includes a first driver 41, the first driver 41 is connected with the ablation optical fiber 5, and the first driver 41 drives the ablation optical fiber 5 to rotate about the major axis of the ablation optical fiber.

There are various structural forms of the first driver 41, including but not limited to a motor, a hydraulic form and a pneumatic form, which is not limited in the embodiment of the present disclosure.

There are various connection forms of the first driver 41 and the ablation optical fiber 5, for example, the rotation driving device 4 may further include a first transmission mechanism, the first driver 41 is connected with the first transmission mechanism, the first transmission mechanism is connected with the ablation optical fiber 5, and thus the first driver 41 drives the ablation optical fiber 5 through connection with the first transmission mechanism to rotate around the major axis of the ablation optical fiber.

There are various structural forms of the first transmission mechanism, including but not limited to a gear form and a belt form.

Thus, through the first driver 41, driving the ablation optical fiber 5 to rotate about the major axis of the ablation optical fiber is implemented.

Continuing to refer to FIG. 4, the rotation driving device 4 may further include a rotation device base 42, and the first driver 41 is mounted on the rotation device base 42.

Figure 5:
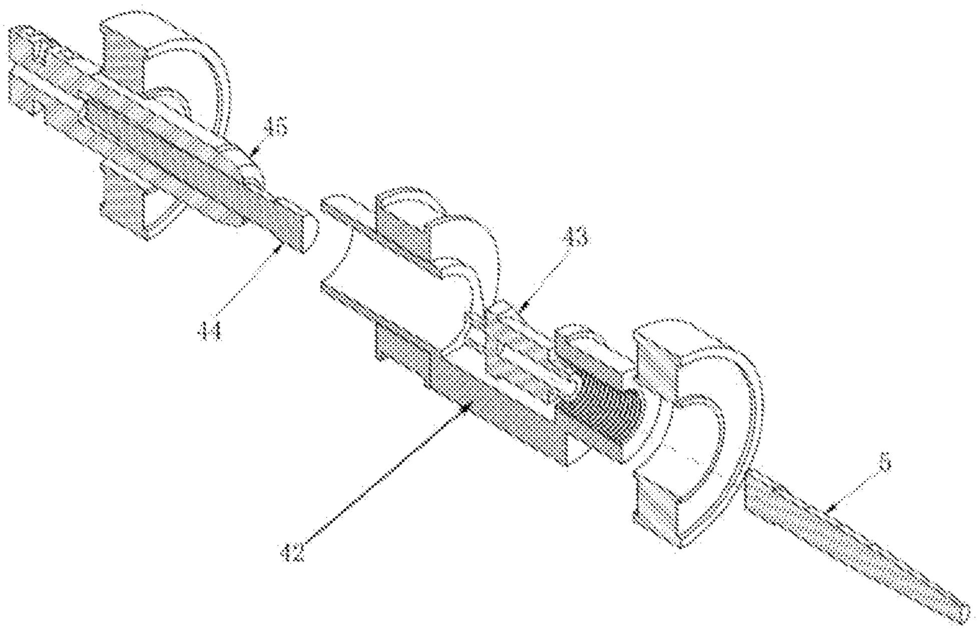
FIG. 5 is a sectional view of a partial structure of FIG. 4.

During use, the ablation optical fiber 5 may be used only with the use of an adapter. FIG. 5 is a sectional view of a partial structure of FIG. 4. Referring to FIG. 5, the rotation driving device 4 may further include an ablation optical fiber adapter 43, and in the use state, the first driver 41 drives the ablation optical fiber adapter 43 to rotate, and the far end of the ablation optical fiber adapter 43 is connected with the ablation optical fiber 5.

The far end of the ablation optical fiber adapter 43 is connected with the ablation optical fiber 5, so that when the first driver 41 drives the ablation optical fiber adapter 43 to rotate, the ablation optical fiber adapter 43 drives the ablation optical fiber 5 to rotate along.

In a case that the rotation driving device 4 includes the first driver 41, the stereotactic driving system provided by the embodiment of the present disclosure further includes a controller, and the first driver 41 is connected in communication with the controller.

In a use state, the controller sends a movement control command to the first driver 41, and the first driver 41 drives the ablation optical fiber 5 according to the movement control command to rotate about the major axis of the ablation optical fiber. In other words, the ablation optical fiber 5 rotating about the major axis of the ablation optical fiber is controlled by the controller. The controller may be an autonomous controller or a signal receiving end. When the controller is the autonomous controller, the movement control command is determined by a stereotactic driving system. When the controller is the signal receiving end, the controller may receive a control signal outside the stereotactic orientation transmission system, for example, the workstation, so that the movement control command is determined according to the received control signal.

There may be various types of the first driver 41. When the first driver 41 is a stepping driver, the first driver 41 directly drives the ablation optical fiber 5 to rotate about the major axis of the ablation optical fiber.

The movement control command may include the target number of rotation times, a terminal point angle position or a relative rotation angle in each time of rotation, a stop duration after each time of rotation and the like, and the first driver 41 drives the ablation optical fiber 5 according to the movement control command to rotate about the major axis of the ablation optical fiber, which may implement:

- the first driver 41 drives the ablation optical fiber 5 to rotate for the target number of rotation times about the major axis of the ablation optical fiber and stop for a stop duration after each time of rotation after reaching the terminal point angle position or the relative rotation angle of this time of rotation.

The terminal point angle position of each time of rotation is determined with an initial angle position as a reference, and the initial angle position may be calibrated.

For example, it is assumed that the target number of rotation times is 2, the initial angle position is a position corresponding to 0°, a terminal point angle position of the first time of rotation is a position corresponding to 30°, a terminal point angle position of the second time of rotation is a position corresponding to 60°, and the stop duration after each time of rotation is 5 s; and the first driver 41 drives the ablation optical fiber 5 to rotate about the major axis of the ablation optical fiber to the terminal point angle position, namely, the position corresponding to 30°, and stop for 5 s, and then the ablation optical fiber 5 is driven to rotate about the major axis of the ablation optical fiber 5 to the terminal point angle position, namely, the position corresponding to 60°, and stop for 5 s. It may be understood that angles and stop positions of many times of rotation may be the same or not, and there may be various combinations of the angles and the stop durations, which all fall within the scope of the present disclosure.

Thus, by arranging the controller, the controller may control the first driver to drive the ablation optical fiber 5 to rotate.

When the first driver 41 is not the stepping motor, a sensor is needed to detect the rotation angle, so in a case that the stereotactic driving system provided by the embodiment of the present disclosure further includes the controller, the rotation driving device 4 further includes a first angle sensor, and the first angle sensor is connected in communication with the controller, for example, the first driver 41 is an ultrasonic motor.

The first angle sensor is connected with a driving shaft of the first driver 41 or the ablation optical fiber 5.

The first angle sensor detects the rotation angle of the ablation optical fiber 5 or a rotation angle of another part the same as the rotation angle of the ablation optical fiber 5, and sends the detected rotation angle to the controller.

When the first driver 41 is not the stepping motor, the first drivers only can rotate or stop rotating, so the first angle sensor is needed to detect the rotation angle of the ablation optical fiber 5 or the rotation angle of another part the same as the rotation angle of the ablation optical fiber 5, and sends the detected rotation angle to the controller, and the controller receives the detected rotation angle so as to know the rotation angle of the ablation optical fiber 5.

There may be various types of another part the same as the rotation angle of the ablation optical fiber 5, including but not limited to the following two types.

First Type:

- the another part may be the driving shaft of the first driver 41.

Second Type:

- in a case that the rotation driving device 4 includes the ablation optical fiber adapter 43, the another part may be the ablation optical fiber adapter 43.

Thus, by means of arranging the first angle sensor, a rotation angle of the driving shaft or the rotation angle of the ablation optical fiber 5 may be detected and fed back to the controller.

Continuing to refer to FIG. 2 and FIG. 3, in a case that the stereotactic driving system provided by the embodiment of the present disclosure includes the controller, the stereotactic driving system provided by the embodiment of the present disclosure further includes an axial movement driving device 6, and the rotation driving device 4 is in sliding connection with the axial movement driving device 6. There are various forms that the rotation driving device 4 is in sliding connection with the axial movement driving device 6, which is not limited in the embodiment of the present disclosure.

The rotation driving device 4 is in sliding connection with the axial movement driving device 6, so the axial movement driving device 6 may drive the rotation driving device 4 to perform axial translation, so that the ablation optical fiber 5 moves with movement of the rotation driving device 4.

In an implementation, the connector 3 may be secured to the axial movement driving device 6, there are various fixed connection forms of the connector 3 and the axial movement driving device 6, for example, continuing to refer to FIG. 2 and FIG. 3, the stereotactic driving system provided by the embodiment of the present disclosure may further include an ancillary part connecting piece 7, one end of the ancillary part connecting piece 7 is securely connected with the axial movement driving device 6, and the other end of the ancillary part connecting piece 7 is securely connected to the connector 3, and thus the connector 3 is securely connected to the axial movement driving device 6 through the ancillary part connecting piece 7.

Thus, the rotation driving device 4 is in sliding connection with the axial movement driving device 6, so the axial movement driving device 6 may drive the rotation driving device 4 to perform axial translation, so that the ablation optical fiber 5 moves with movement of the rotation driving device 4, and thus control over axial translation of the ablation optical fiber 5 is implemented through the axial movement driving device 6.

The axial movement driving device 6 is connected in communication with the controller, and a mode that the axial movement driving device 6 implements control over axial translation of the ablation optical fiber 5 may be:

the controller sends an axial translation instruction to the axial movement driving device 6; and the axial movement driving device 6 drives the rotation driving device 4 to perform axial translation according to the axial translation instruction, so as to drive the ablation optical fiber 5 to perform axial translation.

Specifically, the axial translation instruction may include a translation direction and a translation distance, and the axial movement driving device 6 driving the rotation driving device 4 to perform axial translation according to the axial translation instruction may be:

the axial movement driving device 6 drives the rotation driving device 4 to move for the translation distance in the translation direction.

the translation direction includes front and back, and front and back are preset, for example, the far end is set as front, and the near end is set as back.

Thus, by means of arranging the controller, the controller may control the axial movement driving device 6 to drive the rotation driving device 4 to perform axial translation, so that the ablation optical fiber 5 moves with movement of the rotation driving device 4, and control over axial translation of the ablation optical fiber 5 is achieved.

A structure of the guide device 1 is introduced below.

Figure 6:
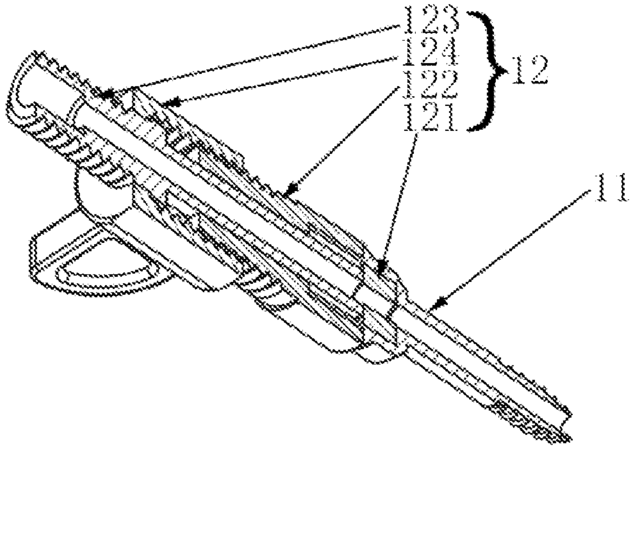
FIG. 6 is a sectional view of an assembled structure of a guide device provided by an embodiment of the present disclosure.
Figure 7:
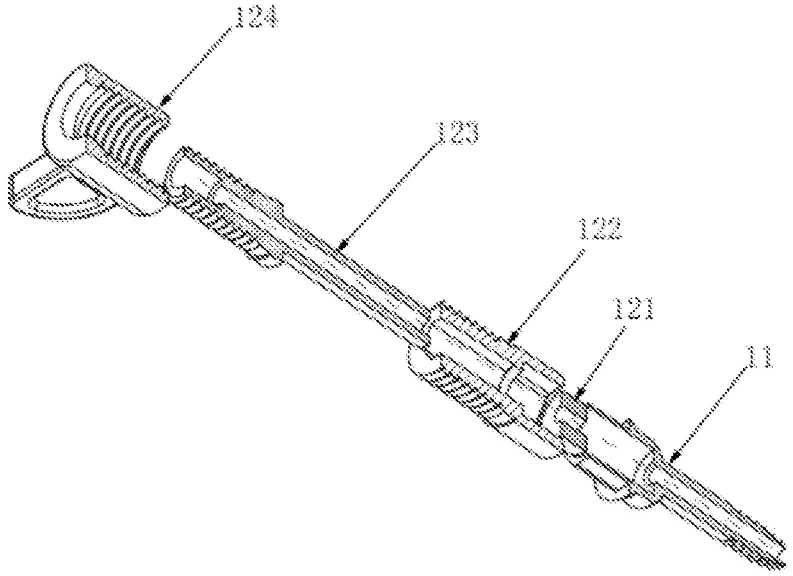
FIG. 7 is a sectional view of an explosive structure of a guide device provided by an embodiment of the present disclosure.

FIG. 6 is a sectional view of an assembled structure of a guide device 1 provided by an embodiment of the present disclosure. FIG. 7 is a sectional view of an explosive structure of a guide device 1 provided by an embodiment of the present disclosure. Referring to FIG. 6 and FIG. 7, the guide device 1 includes a hollow guiding part for a elongated structure 11 and a clamping assembly 12, the far end of the clamping assembly 12 is connected with the near end of the hollow guiding part for the elongated structure 11, and the clamping assembly 12 is configured to fix the relative positions of the sleeve 2 and the hollow guiding part for the elongated structure 11 after the sleeve 2 extends out of the far end of the hollow guiding part for the elongated structure 11.

The hollow guiding part for the elongated structure 11 is hollow and may play a role in guiding and orienting the ablation optical fiber 5. The clamping assembly 12 is an assembly capable of playing a role in clamping.

Thus, by arranging the hollow guiding part for the elongated structure 11 and the clamping assembly 12, the relative positions of the sleeve 2 and the hollow guiding part of the elongated structure 11 can be secured.

Continuing to refer to FIG. 6 and FIG. 7, the clamping assembly 12 may include an elastic plug 121, a clamping adapter 122, a jackscrew 123 and a fastener 124.

The fastener 124 is in threaded connection with the jackscrew 123, the far end of the jackscrew 123 is inserted into the clamping adapter 122 to make contact with the elastic plug 121, the far end of the fastener 124 may be in threaded connection with the clamping adapter 122, the far end of the clamping adapter 122 is connected with the near end of the guiding part 11 of the elongated structure, and the elastic plug 121 is arranged in a cavity of the near end of the hollow guiding part for the hollow elongated structure 11. There are various forms that the far end of the clamping adapter 122 is connected with the near end of the hollow guiding part of the elongated structure 11, may be a threaded connection, or a welding connection or the like, which is not limited in the embodiment of the present disclosure.

The fastener 124 and the jackscrew 123 may be of an integrated structure, and the integrated structure is in threaded connection with the clamping adapter 122.

In a use state, namely, a state shown in FIG. 6, the fastener 124 is tightened to the jackscrew 123 and the clamping adapter 122, the jackscrew 123 tightly compresses the elastic plug 121, the sleeve 2 penetrates through the jackscrew 123, the elastic plug 121 and the hollow guiding part for the elongated structure 11, the far end of the sleeve 2 extends out of the far end of the hollow guiding part for the elongated structure 11, as the jackscrew 123 tightly compresses the elastic plug 121, the elastic plug 121 squeezes the sleeve 2 inside, and further, a position of the sleeve 2 is secured through the elastic plug 121. For example, the elastic plug 121 may be a rubber plug.

Thus, by inserting the far end of the jackscrew 123 into the clamping adapter 122 to make contact with the elastic plug 121, when the fastener 124 is tightened to the jackscrew 123 and the clamping adapter 122, the jackscrew 123 may tightly compress the elastic plug 121, so the elastic plug 121 squeezes the sleeve 2 inside, and thus a purpose of fixing the sleeve 2 is achieved.

A structure of the connector 3 is introduced below.

Figure 8:
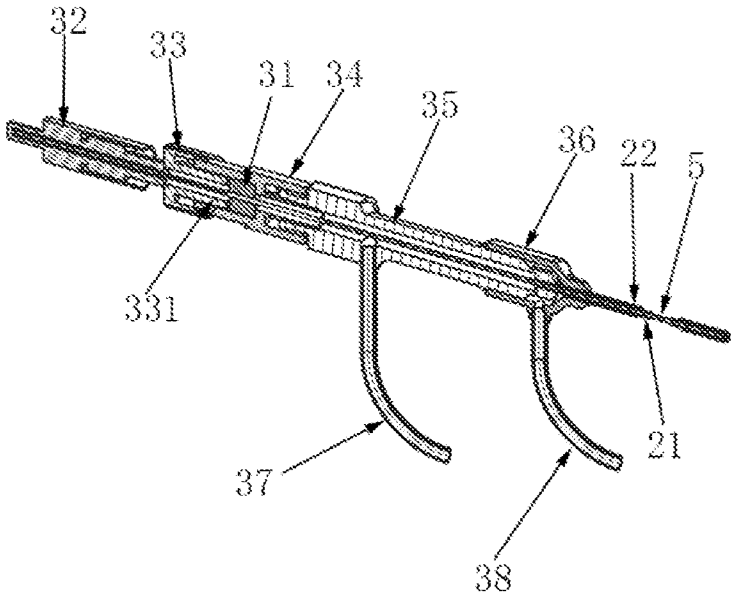
FIG. 8 is a schematic diagram of an assembled structure of a connector provided by an embodiment of the present disclosure.
Figure 9:
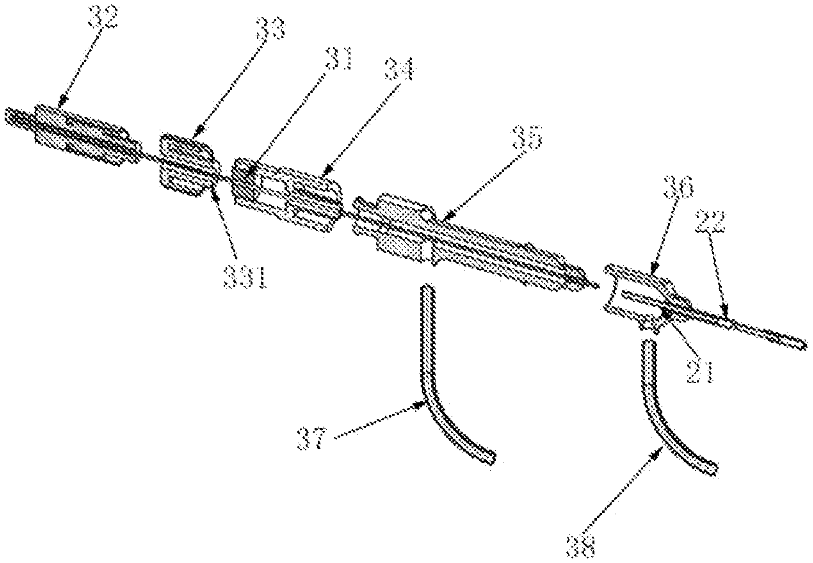
FIG. 9 is a schematic structural explosive view of a connector provided by an embodiment of the present disclosure.

FIG. 8 is a schematic diagram of an assembled structure of a connector 3 provided by an embodiment of the present disclosure. FIG. 9 is a schematic structural explosive view of a connector 3 provided by an embodiment of the present disclosure. Referring to FIG. 6 and FIG. 7, the connector 3 may include a sealing plug 31, an ablation optical fiber connector 32, and in sequence from near end to far end, a sealing nut 33, a Luer taper 34, a water inlet adapter 35, and a water outlet adapter 36.

The sealing plug 31 is arranged in the Luer taper 34, and an internal protrusion 331 of the sealing nut 33 makes contact with the sealing plug 31.

In a use state, the sealing nut 33 is tightened to the Luer taper 34, the internal protrusion 331 of the sealing nut 33 tightly compresses the sealing plug 31, and the ablation optical fiber 5 is arranged within the inside lumen of the ablation optical fiber connector 32, the sealing nut 33, the sealing plug 31 and the water inlet adapter 35 to enter the sleeve 2.

The ablation optical fiber connector 32 is connected with a transmission part of the rotation driving device 4, so that the ablation optical fiber 5 in the ablation optical fiber connector 32 moves together with the ablation optical fiber connector 32. The transmission part of the rotation driving device 4 may be the ablation optical fiber adapter 43. The sealing nut 33 is in threaded connection with the Luer taper 34. The Luer taper 34 is in threaded connection with the water inlet adapter 35. A connection mode of the water inlet adapter 35 and the water outlet adapter 36 may be a threaded connection, or a welded connection or a gluing connection, which is not limited in the embodiment of the present disclosure.

During use, the sealing nut 33 is tightened to the Luer taper 34, so that the internal protrusion 331 of the sealing nut 33 tightly compresses the sealing plug 31, the sealing plug 31 squeezes the ablation optical fiber 5 inside, a cooling fluid is prevented from flowing out, but this squeezing does not affect rotation and movement of the ablation optical fiber 5.

Thus, by means of arranging the sealing plug 31, the ablation optical fiber connector 32, and in sequence from near end to far end, the sealing nut 33, the Luer taper 34, the water inlet adapter 35, and the water outlet adapter 36, sealing of the ablation optical fiber 5 is implemented.

During use, the ablation optical fiber 5 needs cooling and sealing, so, in order to implement cooling and sealing for the ablation optical fiber 5, continuing to refer to FIG. 8 and FIG. 9, the connector 3 may further include a first water pipe 37 and a second water pipe 38, the sleeve 2 may include an internal water circulation pipe 21 and an external circulation pipe 22, the first water pipe 37 may be a water inlet pipe or a water outlet pipe, likewise, the second water pipe 38 may be a water inlet pipe or a water outlet pipe, but if one is a water outlet pipe, the other one is a water inlet pipe, and functions of the water inlet adapter 35 and the water outlet adapter 36 may be interchangeable. In other words, the water inlet adapter 35 may be used for water entry or water exit, the water outlet adapter 36 may be used for water entry or water exit, but if one is used for water entry, the other one is used for water exit.

The internal water circulation pipe 21 is arranged in the external water circulation pipe 22, a gap exists between the two, the first water pipe 37 communicates with the internal water circulation pipe 21 via the water inlet adapter 35, and the second water pipe 38 communicates with the external water circulation pipe 22 via the water outlet adapter 36.

In a use state, the ablation optical fiber 5 is arranged through the inside lumen of the ablation optical fiber connector 32, the sealing nut 33 and the sealing plug 31 to enter the internal water circulation pipe 21.

During use, cooling liquid is conveyed through one of the first water pipe 37 or the second water pipe 38, the cooling liquid passes through the gap between the internal water circulation pipe 21 and the external water circulation pipe 22, the cooling liquid is outputted from the other one of the first water pipe 37 and the second water pipe 38, thus, the cooling liquid may play a role in cooling the ablation optical fiber 5 in the internal water circulation pipe 21, and the sealing plug 31 plays a role in cooling and sealing the ablation optical fiber 5.

Thus, by means of arranging the sealing plug 31, making the connector 3 include the first water pipe 37 and the second water pipe 38 and making the sleeve 2 include the internal water circulation pipe 21 and the external water circulation pipe 22, cooling sealing for the ablation optical fiber 5 is implemented.

A friction may exist between the sealing plug 31 and the ablation optical fiber 5 and affects rotation of the ablation optical fiber 5, so in order to avoid occurrence of this situation, a rigid structure may be arranged on an outside of at least the first portion of the ablation optical fiber 5, or at least the first portion of the ablation optical fiber 5 has an external surface structure with enhanced strength, where the first portion includes a portion of the ablation optical fiber 5 which begins from the proximal end to the inside of the sealing plug 31 and a portion of the ablation optical fiber which exceeds the far end of the sealing plug 31, and when the far end of the ablation optical fiber 5 is located at the farthest end of the system, the length of the portion exceeding the far end of the sealing plug 31 is greater than the translation movement range of the ablation optical fiber 5.

During use, the ablation optical fiber 5 is not secured but may move front and back. When the ablation optical fiber 5 moves front, the translation movement range of the ablation optical fiber 5 is a front movement distance. When the ablation optical fiber 5 moves back, the movement distance of the ablation optical fiber 5 is a back retreat distance. A front-back direction may be obtained through calibration, for example, a direction where the far end is located is calibrated as front, and a direction where the near end is located is calibrated as back.

When the far end of the ablation optical fiber 5 is located at the farthest end of the system, the length of the portion exceeding the sealing slug 31 is set to be greater than the movement distance of the ablation optical fiber 5, so that it may be guaranteed that the sealing plug 31 may make contact with the first portion of the ablation optical fiber 5 all the time during front-back movement of the ablation optical fiber 5.

Thus, by means of making at least the first portion of the ablation optical fiber 5 have the rigid structure or the external surface structure with enhanced strength, a strength of the ablation optical fiber 5 is enhanced, and by means of making the first portion include a portion of the ablation optical fiber 5 which begins from the proximal end to the inside of the sealing plug 31 and a portion of the ablation optical fiber which exceeds the far end of the sealing plug 31, and making the length of the portion exceeding the sealing plug 31 greater than the movement distance of the ablation optical fiber 5 when the far end of the ablation optical fiber 5 is located at the farthest end of the system, it is guaranteed that the ablation optical fiber 5 located in the sealing plug 31 still has the rigid structure or the external surface structure with enhanced strength even after the ablation optical fiber 5 moves, and an influence of the friction between the sealing plug 31 and the ablation optical fiber 5 to rotation of the ablation optical fiber 5 is eliminated.

Besides, when the rotation driving device 4 includes the first angle sensor, the rotation angle of the ablation optical fiber 5 having the rigid structure or the external surface structure with enhanced strength may be detected and sent to the controller, so that the rotation angle of the ablation optical fiber 5 is accurately monitored and control over the rotation of the ablation optical fiber 5 is implemented.

Figure 10:
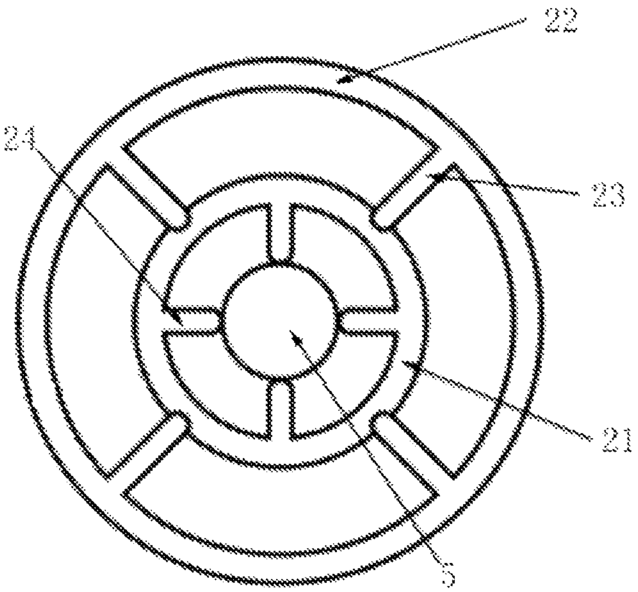
FIG. 10 is a schematic structural diagram of a sleeve provided by an embodiment of the present disclosure.

FIG. 10 is a schematic structural diagram of a sleeve 2 provided by an embodiment of the present disclosure. Referring to FIG. 10, in order to enhance a strength of the sleeve 2, a first strength enhancing structure 23 may be further arranged between the external water circulation pipe 22 and the internal water circulation pipe 21, and a second strength enhancing structure 24 is arranged between the internal water circulation pipe 21 and the ablation optical fiber 5.

The first strength enhancing structure 23 may be a plurality of enhancing frames, and the plurality of enhancing frames may be uniformly distributed between the external water circulation pipe 22 and the internal water circulation pipe 21. Likewise, the second strength enhancing structure 24 may also be a plurality of enhancing frames, and the plurality of enhancing frames may be uniformly distributed between the internal water circulation pipe 21 and the ablation optical fiber 5.

In order to prevent the second strength enhancing structure 24 from affecting the rotation of the ablation optical fiber 5, a gap exists between the second strength enhancing structure 24 and the ablation optical fiber 5, and a surface of the enhancing frames possibly making contact with the ablation optical fiber 5 is set as a convex surface.

Thus, by means of arranging the first strength enhancing structure 23 and the second strength enhancing structure 24, the strength and puncture capacity of the sleeve 2 are improved, and a situation that deformation is caused by squeezing of an external force and circulation of a cooling fluid is blocked is prevented.

The axial movement driving device 6 is introduced below.

Figure 11:
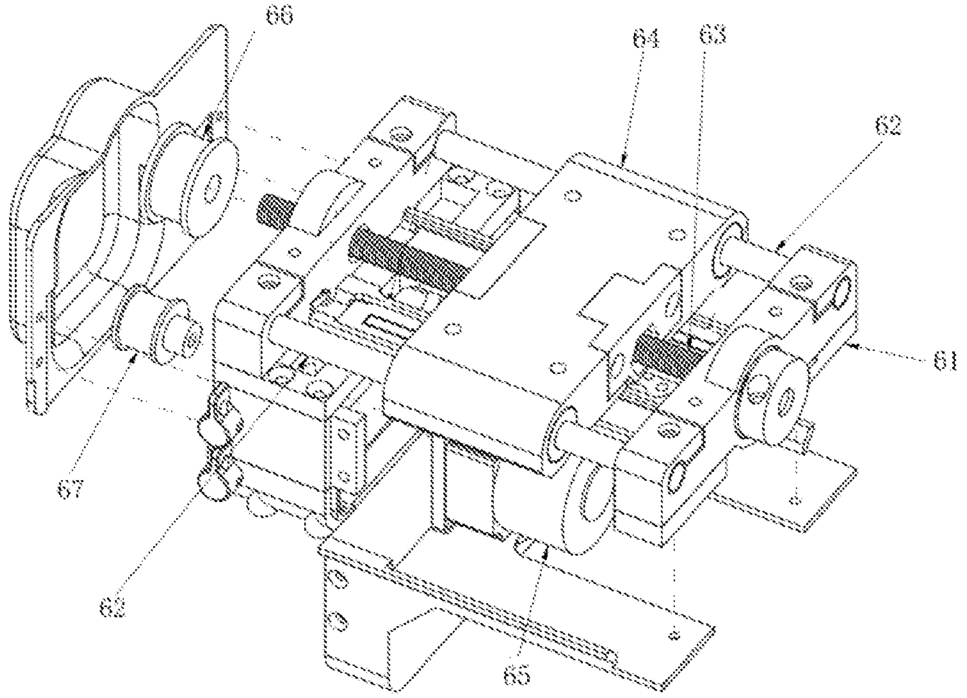
FIG. 11 is schematic structural diagram of an axial movement driving device provided by an embodiment of the present disclosure.

FIG. 11 is a schematic structural diagram of an axial movement driving device 6 provided by an embodiment of the present disclosure. Referring to FIG. 11, the axial movement driving device 6 may include an axial movement driving device base 61, at least one sliding rail 62, a lead screw 63, a sliding block 64 and a second driver 65.

At least one sliding rail 62 and the lead screw 63 are arranged in parallel and is arranged through the sliding block 64, the two ends of the at least one sliding rail 62 are securely mounted on the axial movement driving device base 61, the lead screw 63 is connected to the axial movement driving device base 61, the second driver 65 drives the lead screw 63 to rotate, the second driver 65 is mounted on the axial movement driving device base 61, and the rotation driving device 4 is mounted on the sliding block 64.

During use, the second driver 65 drives the lead screw 63 to rotate, the lead screw 63 drives the sliding block 64 to move along the sliding rail, and as the rotation driving device 4 is mounted on the sliding block 64, the sliding block 64 may drive the rotation driving device 4 to move front and back.

There are various structural forms of the second driver 65, including but not limited to a motor, a hydraulic form and a pneumatic form, which is not limited in the embodiment of the present disclosure.

There are various connection forms of the second driver 65 and the lead crew 63, for example, the axial movement driving device 6 may further include a second transmission mechanism, the second driver 65 is connected with the second transmission mechanism, the second transmission mechanism is connected with the other end of the lead crew 63, and thus the second driver 65 drives the lead screw 63 to rotate through connection with the second transmission mechanism.

There are various structural forms of the second transmission mechanism, including but not limited to a gear form and a belt form.

For example, continuing to refer to FIG. 11, the second transmission mechanism includes a driven wheel 66, a driving wheel 67 and a belt. The second driver 65 drives the driving wheel 67 to rotate, the driving wheel 67 is connected with the driven wheel 66 through the belt, the driving wheel 67 drives the driven wheel 66 to rotate, the driven wheel 66 is connected with the other end of the lead screw 63, and the driven wheel 66 drives the lead screw 63 to rotate.

Thus, by means of arranging the sliding rail 62, the lead screw 63, the sliding block 64 and the second driver 65, the sliding block 64 may drive the rotation driving device 4 to move front and back.

It needs to be noted that the above embodiments may be combined at random.

Embodiment 2

A second type of magnetic resonance guided laser ablation treatment system in the present disclosure includes: a workstation 100, a laser ablation apparatus 200, a stereotactic driving system 300 and an optical fiber cooling assembly 400. The optical fiber cooling assembly 400 is described separately rather than described as a part of the stereotactic driving system 300, and during use, the ablation optical fiber is arranged in the optical fiber cooling assembly 400.

Another structure of the stereotactic driving system in the embodiment is introduced below.

Figure 12:
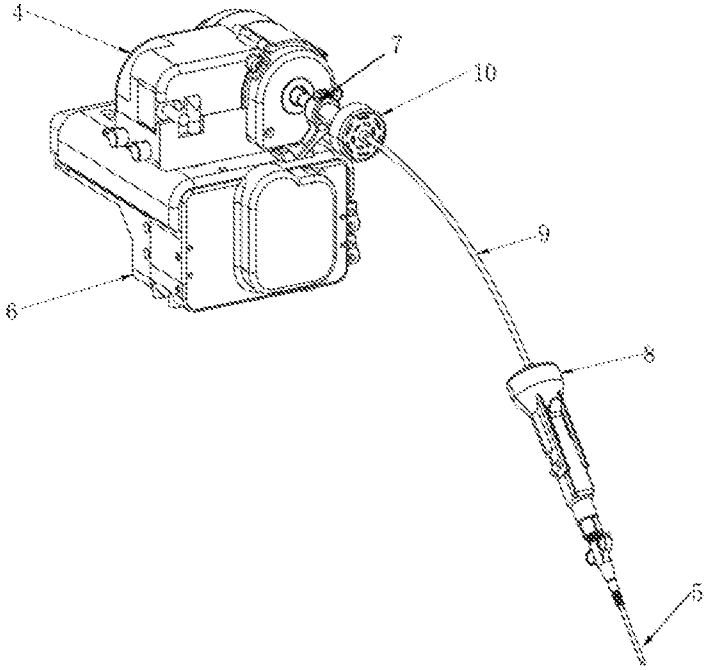
FIG. 12 is a schematic structural diagram of a second type of stereotactic driving system provided by an embodiment of the present disclosure.

FIG. 12 is a schematic structural diagram of a second type of stereotactic driving system provided by an embodiment of the present disclosure. Referring to FIG. 12, the stereotactic driving system provided by the embodiment of the present disclosure includes: a guiding device 8, a transmission sleeve 9, an ancillary part 10 and a rotation driving device 4.

The guiding device 8 is connected with the far end of the transmission sleeve 9, and the near end of the transmission sleeve 9 is connected with the far end of the ancillary part 10.

In a use state, the ablation optical fiber is arranged through the ancillary part 10, the transmission sleeve 9 and the guiding device 8, and the far end of the ablation optical fiber may extend out from the far end of the guiding device 8, and the rotation driving device 4 drives the ablation optical fiber to rotate.

The ancillary part 10 may be secured to any structure as long as the near end of the ancillary part 10 is opposite to the far end of the rotation driving device 4 after fixing, so that the rotation driving device 4 may drive the ablation optical fiber to rotate, and the ablation optical fiber 5 may, in the ancillary part 10, move in an axial direction of the ablation optical fiber and rotate about the major axis of the ablation optical fiber. For example, the ancillary part 10 is secured to a special support.

To sum up, the stereotactic driving system provided by the embodiment of the present disclosure includes the guiding device 8, the transmission sleeve 9, the ancillary part 10 and the rotation driving device 4. The guiding device 8 is connected with the far end of the transmission sleeve 9, and the near end of the transmission sleeve 9 is connected with the far end of the ancillary part 10. In a use state, the ablation optical fiber 5 is arranged within the ancillary part 10, the transmission sleeve 9 and the guiding device 8, the far end of the ablation optical fiber may extend out from the far end of the guiding device 8, and the rotation driving device 4 drives the ablation optical fiber to rotate. In the embodiment of the present disclosure, the rotation driving device drives the ablation optical fiber to rotate so as to achieve control over rotation of the ablation optical fiber, an implantation direction of the ablation optical fiber may be guided through the guiding device, orientation control over the ablation optical fiber may be achieved without additionally mounting a supporting structure at a skull, suffering of a patient is relieved, and mounting is simple and convenient.

Continuing to refer to FIG. 12, the stereotactic driving system provided by the embodiment of the present disclosure may further include an axial movement driving device 6, the rotation driving device 4 is in sliding connection with the axial movement driving device 6, and there are various forms that the rotation driving device 4 is in sliding connection with the axial movement driving device 6, which is not limited in the embodiment of the present disclosure. The rotation driving device 4 is in sliding connection with the axial movement driving device 6, so the axial movement driving device 6 may drive the rotation driving device 4 to move in a length direction of the ablation optical fiber, so that the ablation optical fiber moves with movement of the rotation driving device 4.

The ancillary part 10 may be further secured to the axial movement driving device 6, there are various fixed connection forms of the ancillary part 10 and the axial movement driving device 6, for example, continuing to refer to FIG. 12, the stereotactic driving system provided by the embodiment of the present disclosure may further include an ancillary part connecting piece 7, one end of the ancillary part connecting piece 7 is securely connected with the axial movement driving device 6, and the other end of the ancillary part connecting piece is securely connected with the ancillary part 10, and thus the ancillary part 10 is securely connected with the axial movement driving device 6 through the ancillary part connecting piece 7.

Thus, the rotation driving device 4 is in sliding connection with the axial movement driving device 6, so the axial movement driving device 6 may drive the rotation driving device 4 to move front and back in the length direction of the ablation optical fiber, so that the ablation optical fiber moves with movement of the rotation driving device 4, and thus control over movement of the ablation optical fiber in the length direction is implemented through the axial movement driving device.

Various parts of the stereotactic driving system are introduced in detail below.

Figure 13:
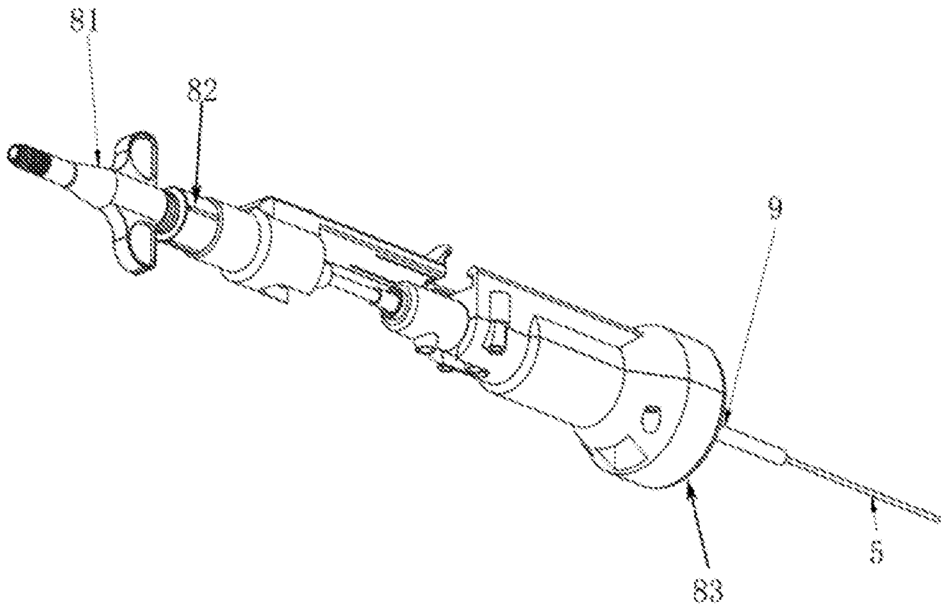
FIG. 13 is a schematic structural diagram of a guiding device provided by an embodiment of the present disclosure.

FIG. 13 is a schematic structural diagram of a guiding device 8 provided by an embodiment of the present disclosure. Referring to FIG. 13, the guiding device 8 includes a hollow guide part for a elongated structure 81 and a guiding device shell, the near end of the hollow guide part for a elongated structure 81 is connected with the far end of the guiding device shell, and the near end of the guiding device shell is connected with the far end of the transmission sleeve 9.

The ablation optical fiber is arranged within the inside lumen of the guiding device shell and the hollow guide part for a elongated structure 81, and the far end of the ablation optical fiber 5 may extend out of the far end of hollow guide part for a elongated structure 81.

The hollow guide part for a elongated structure 81 is hollow and may play a role in guiding and orienting the ablation optical fiber. For example, the hollow guide part for a elongated structure 81 may be a hollow bone screw.

There are various structure forms of the guiding device shell, including but not limited to the following several types.

First Type:

the guiding device shell is a first bone screw cap, the near end of the hollow guide part for a elongated structure 81 is in threaded connection with the far end of the first bone screw cap, and the near end of the first bone screw cap is connected with the far end of the transmission sleeve 9.

In a case that the guiding device shell is the first bone screw cap, the guiding device 8 may further include a second angle sensor and a second rotation locating device, both the second angle sensor and the second rotation locating device are mounted on the guiding device shell, namely, in the first bone screw cap, and the ablation optical fiber is arranged within the second rotation locating device and the second angle sensor.

Specifically, the second angle sensor is detachably connected with the second rotation locating device, and the ablation optical fiber is arranged within the second rotation locating device and the second angle sensor and may move in the axial direction and rotate about the major axis of the ablation optical fiber. In a use state, the second rotation locating device clamps the ablation optical fiber according to a preset pressure and allows the ablation optical fiber to move in the length direction of the ablation optical fiber, meanwhile, the ablation optical fiber is caused to drive the second rotation locating device to rotate, and the second angle sensor detects a rotation angle of the second rotation locating device; and as the ablation optical fiber drives the second rotation locating device to rotate, the rotation angle of the second rotation locating device detected by the second angle sensor is a rotation angle of the ablation optical fiber, and the second angle sensor sends the detected rotation angle to a control device.

Thus, by means of arranging the second rotation locating device and the second angle sensor, a rotation angle of the ablation optical fiber located in the guiding device shell may be detected.

A structure of the second rotation locating device is introduced below.

Figure 14:
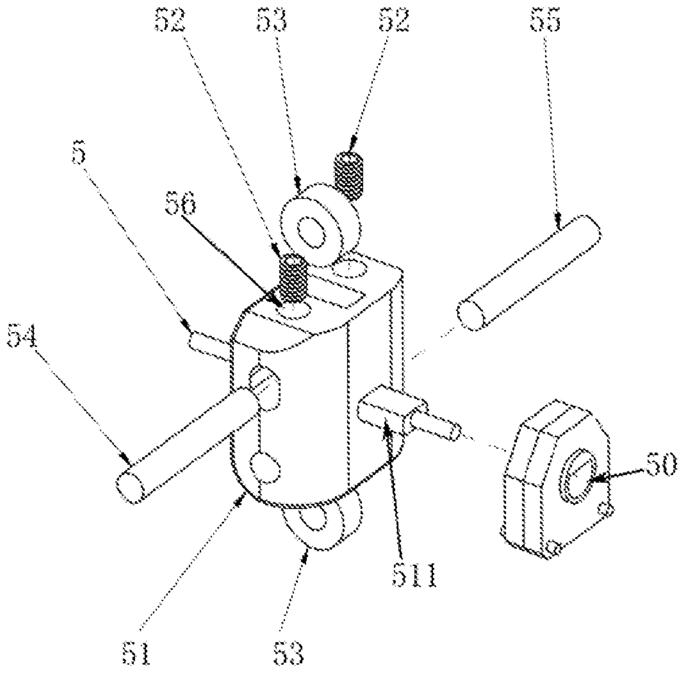
FIG. 14 is an explosive view of an angle of a second rotation orientation device and a second angle sensor provided by an embodiment of the present disclosure.
Figure 15:
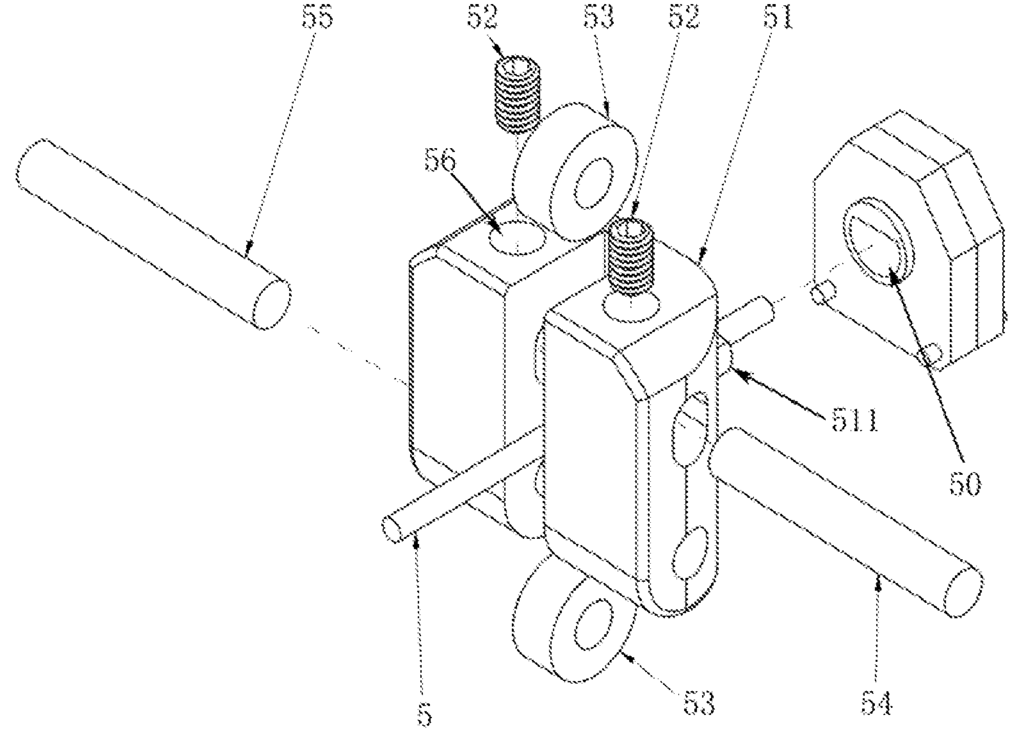
FIG. 15 is an explosive view of another angle of a second rotation orientation device and a second angle sensor provided by an embodiment of the present disclosure.

FIG. 14 is an explosive view of an angle of a second rotation locating device and a second angle sensor provided by an embodiment of the present disclosure. FIG. 15 is an explosive view of another angle of a second rotation locating device and a second angle sensor provided by an embodiment of the present disclosure. Referring to FIG. 14 to FIG. 15, the second rotation locating device may include a main body 51, at least one adjustable jacking press 52, two bearings 53, a first shaft 54 and a second shaft 55.

Two holes are formed in a side surface of the main body 51, a groove is formed in one end of the main body 51 and divides the two holes into two portions respectively, a through hole is formed in a groove bottom of the groove, a first hole 56 matching the adjustable jacking press 52 is formed in an end surface of the main body 51, one of the two holes close to the first hole 56 communicates with the first hole 56, the two bearings 53 are arranged in the groove, the first shaft 54 penetrates through one of the two bearings 53 to be arranged in one of the two holes, the second shaft 55 penetrates through the other one of the two bearings 53 to be arranged in the other one of the two holes, the adjustable jacking press 52 is arranged in the first hole 56, and the ablation optical fiber 5 is arranged between the two bearings 53 and arranged within the through hole of the groove bottom.

For example, center lines of the two holes are parallel to each other.

In a use state, the adjustable jacking press 52 is tightened, the two bearings 53 clamp the ablation optical fiber 5, a pressure between the two bearings 53 and the ablation optical fiber 5 reaches a preset value, in other words, a position of the shaft in one hole of the two holes communicating with the first hole 56 may be adjusted by tightening the adjustable jacking press 52, the shaft in the hole communicating with the first hole 56 drives the bearing 53 penetrated thereby to exert a pressure on the ablation optical fiber 5, meanwhile, the shaft in the other hole of the two holes not communicating with the first hole 56 also exerts a pressure on the ablation optical fiber 5 through the bearing 53 penetrated thereby, and thus by means of tightening the adjustable jacking press 52, the pressure between the two bearings 53 and the ablation optical fiber 5 is adjusted to the preset value.

In order to adjust the position of the shaft in one hole of the two holes communicating with the first hole 56 by tightening the adjustable jacking press 52, a size of the hole of the two holes communicating with the first hole 56 needs to be set to be greater than a size of the shaft therein.

The shaft in the hole of the two holes not communicating with the first hole 56 may be securely arranged in the hole, which is not limited in the embodiment of the present disclosure as long as the shaft in the hole may exert the pressure on the ablation optical fiber 5 through the bearing 53 penetrated thereby.

A type of the bearings 53 is not limited in the embodiment of the present disclosure, for example, the bearing 53 may be a bush.

For example, the number of adjustable jacking presses 52 may be two, and the number of first holes 56 may be two. The two first holes 56 may be formed in two sides of the groove separately.

Continuing to refer to FIG. 14 to FIG. 15, in a case that the second rotation locating device includes the main body 51, at least one adjustable jacking press 52, the two bearings 53, the first shaft 54 and the second shaft 55, a protrusion 511 is arranged at the other end of the main body 51, a through hole is formed in the protrusion 511, the through hole of the protrusion 511 communicates with the through hole of the groove bottom, the ablation optical fiber 5 is arranged within the through hole of the protrusion 511, the second angle sensor is provided with a clamping hole 50, and the protrusion 511 is clamped with the clamping hole 50.

A detachable connection form of the second angle sensor and the second rotation locating device may be that the protrusion 511 is arranged at the other end of the main body 51, the clamping hole 50 is formed in the second angle sensor, and the protrusion 511 is clamped with the clamping hole 50, so the second angle sensor is connected with the second rotation locating device.

In an implementation, a left side and right side of the protrusion 511 are arc-shaped, the clamping hole 50 of the second angle sensor is in a horseshoe shape, the protrusion 511 is clamped with the horseshoe-shaped clamping hole 50, and certainly, the embodiment of the present disclosure does not limit specific shapes of the protrusion 511 and the clamping hole 50 as long as the two may be clamped.

Thus, the protrusion 511 is arranged at the other end of the main body 51, and the clamping hole 50 is formed in the second angle sensor, so the second angle sensor is detachably connected with the second rotation locating device.

Second Type:

Continuing to refer to FIG. 13, the guiding device shell may include a second bone screw cap 82, a guiding device shell body and a transmission sleeve mounting base 83.

The near end of the hollow guide part for a elongated structure 81 is in threaded connection with the far end of the second bone screw cap 82, the near end of the second bone screw cap 82 is connected with the far end of the guiding device shell body, the transmission sleeve mounting base 83 is arranged at the near end of the guiding device shell body, the transmission sleeve mounting base 83 is connected with the far end of the transmission sleeve 9, and the ablation optical fiber 5 is arranged within the transmission sleeve mounting base 83, the guiding device shell body and the second bone screw cap 82.

During use, first, the near end of the second bone screw cap 82 is connected with the far end of the guiding device shell body, the transmission sleeve mounting base 83 is arranged at the near end of the guiding device shell body, the transmission sleeve mounting base 83 is connected with the far end of the transmission sleeve 9, and then the far end of the second bone screw cap 82 is in threaded connection with the near end of the hollow guide part for a elongated structure 81.

The guiding device shell body and the transmission sleeve mounting base 83 may be of an integrated structure or not, which is not limited in the embodiment of the present disclosure.

Figure 16:
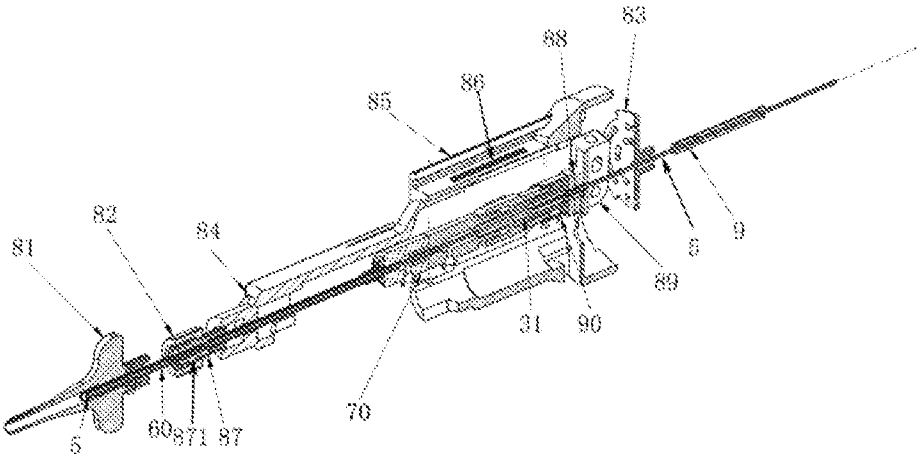
FIG. 16 is a sectional view of FIG. 13.

When the guiding device shell body is not of the integrated structure, for example, FIG. 16 is a sectional view of FIG. 13, referring to FIG. 13 and FIG. 16, the guiding device shell body may include a guiding device shell body fixed portion 84 and a guiding device shell body sliding portion 85, the near end of the second bone screw cap 82 is connected with the far end of the guiding device shell body fixed portion 84, a near end of the guiding device shell body fixed portion 84 is connected with the far end of the guiding device shell body sliding portion 85, the transmission sleeve mounting base 83 is arranged at the near end of the guiding device shell body sliding portion 85, and the ablation optical fiber 5 is arranged within the guiding device shell body sliding portion 85 and the guiding device shell body fixed portion 84.

Continuing to refer to FIG. 16, the guiding device shell body fixed portion 84 and/or the guiding device shell body sliding portion 85 are/is provided a graduated scale 86, the guiding device shell body fixed portion 84 and the guiding device shell body sliding portion 85 may move relative to each other, the graduated scale 86 displays a distance of the relative movement, in other words, during use, the guiding device shell body sliding portion 85 may be pulled away from the guiding device shell body fixed portion 84, a pulling distance may be read from the graduated scale 86 when each distance is pulled, and in FIG. 16, the guiding device shell body sliding portion 85 is provided with the graduated scale 86.

Thus, by means of arranging the graduated scale 86 on the guiding device shell body fixed portion 84 and/or the guiding device shell body sliding portion 85, the distance of the relative movement between the guiding device shell body fixed portion 84 and the guiding device shell body sliding portion 85 may be displayed.

Continuing to refer to FIG. 16, on the basis that the guiding device shell includes the second bone screw cap 82, the guiding device shell body and the transmission sleeve mounting base 83, the guiding device shell further includes a bone screw adapter bolt 87, the second bone screw cap 82 is tightened to the hollow guide part for a elongated structure 81, the far end of the bone screw adapter bolt 87 is secured into the second bone screw cap 82, the near end of the bone screw adapter bolt 87 is in threaded connection with the far end of the guiding device shell body, and the ablation optical fiber 5 is arranged within the bone screw adapter bolt 87.

Specifically, a bolt protrusion 871 is arranged on the bone screw adapter bolt 87, a size of the bolt protrusion 871 is greater than a size of an opening of the near end of the second bone screw cap 82, and when the second bone screw cap 82 is tightened to the hollow guide part for a elongated structure 81, the opening of the near end of the second bone screw cap 82 clamps the bolt protrusion 871, so that the far end of the bone screw adapter bolt 87 is secured into the second bone screw cap 82.

During use, first, the bone screw adapter bolt 87 is inserted into the second bone screw cap 82, then the near end of the bone screw adapter bolt 87 is in threaded connection with the far end of the guiding device shell body, and finally, the second bone screw cap 82 is tightened to the hollow guide part for a elongated structure 81, so that the opening of the near end of the second bone screw cap 82 and the hollow guide part for a elongated structure 81 clamp the bolt protrusion 871.

Continuing to refer to FIG. 13, in a case that the guiding device shell is the above second structure, the guiding device 8 may further include a second angle sensor 88 and a second rotation locating device 89, both the second angle sensor 88 and the second rotation locating device 89 are mounted in the guiding device shell, and the ablation optical fiber 5 is arranged within the inside lumen of the second rotation locating device 89 and the second angle sensor 88. Specific structures and connection forms of the second rotation locating device 89 and the second angle sensor 88 refer to corresponding description when the guiding device shell is the above first structure, which is not repeated here.

During use, the ablation optical fiber needs to be cooled, so continuing to refer to FIG. 16, the guiding device 8 may further include a cooling sleeve 60, a cooling circulation assembly 70 and a sealing plug 31, the cooling circulation assembly 70 and the sealing plug 31 are mounted in the guiding device shell in sequence from far end to near end, the cooling sleeve 60 penetrates through the sealing plug 31 and the cooling circulation assembly 70 in sequence, and the ablation optical fiber 5 is arranged in the cooling sleeve 60.

There are various sealing forms, in an implementation, the guiding device 8 may further include a cooling circulation assembly cap 90, the cooling circulation assembly cap 90 is arranged at the near end of the sealing plug 31 and mounted in the guiding device shell, and the cooling sleeve 60 penetrates through the cooling circulation assembly cap 90.

Thus, by means of arranging the cooling sleeve 60, the cooling circulation assembly 70 and the sealing plug 31, cooling sealing for the ablation optical fiber is implemented.

The cooling circulation assembly 70 is clamped in the guiding device shell body sliding portion 85, and the cooling sleeve 60 may be driven to perform axial movement for a fixed distance through the guiding device shell body sliding portion 85 relative to the guiding device shell body fixed portion 84.

A structure of the ancillary part 10 is introduced below.

Figure 17:
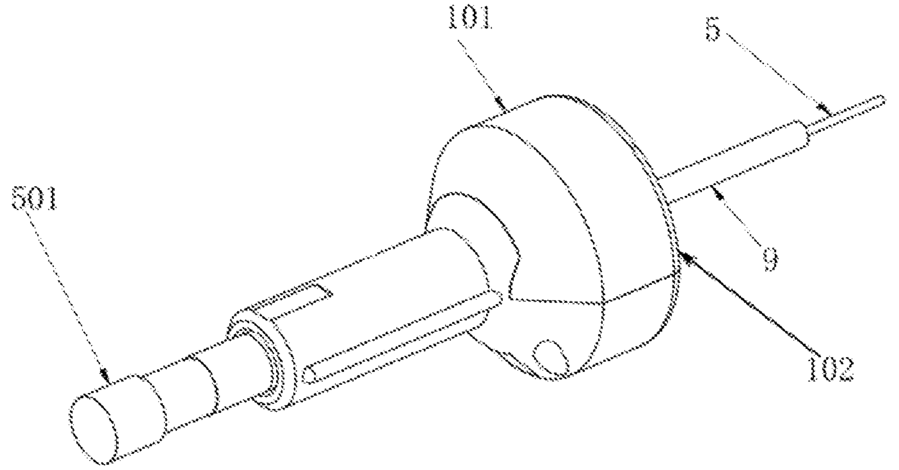
FIG. 17 is a schematic structural diagram of an ancillary part.

FIG. 17 is a schematic structural diagram of an ancillary part 10. Referring to FIG. 17, the ancillary part 10 may include an ancillary part shell 101 and an ancillary part transmission sleeve mounting base 102. The ancillary part transmission sleeve mounting base 102 is arranged at the far end of the ancillary part shell 101, the ancillary part transmission sleeve mounting base 102 is connected with the near end of the transmission sleeve 9, the ablation optical fiber 5 is arranged within the ancillary part shell 101 and the ancillary part transmission sleeve mounting base 102, the ablation optical fiber 5 is provided with an ablation optical fiber plug 501, and the ablation optical fiber plug 501 may extend out from the near end of the ancillary part shell 101. In an implementation, the ancillary part shell 101 and the ancillary part transmission sleeve mounting base 102 may be of an integrated structure.

Figure 18:
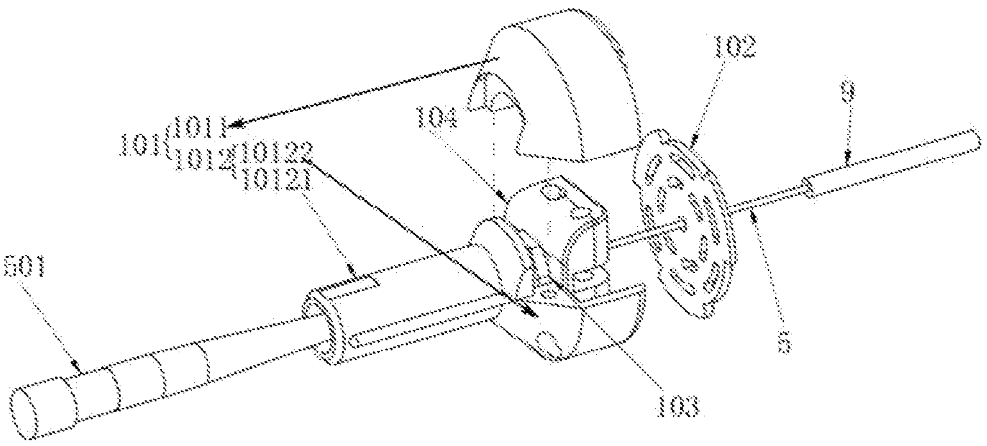
FIG. 18 is another schematic structural diagram of an ancillary part.

FIG. 18 is another schematic structural diagram of an ancillary part 10. Referring to FIG. 18, in a case that the guiding device 8 includes the sealing plug 31, a friction force between the sealing plug 31 and the ablation optical fiber 5 and a stress of the ablation optical fiber 5 in an axial direction are accumulated, consequently, the rotation angle of the ablation optical fiber 5 at the second angle sensor is unstable after reaching a preset requirement, so in a case that the guiding device 8 further includes the cooling sleeve 60, the cooling circulation assembly 70 and the sealing plug 31, the ancillary part 10 may further include a third angle sensor 103 and a third rotation locating device 104, both the third rotation locating device 104 and the third angle sensor 103 are mounted in the ancillary part shell 101, and the ablation optical fiber 5 is arranged within the inside lumen of the third rotation locating device 104 and the third angle sensor 103. Specific structures and connection forms of the third rotation locating device 104 and the third angle sensor 103 are the same as specific structures and connection forms of the second rotation locating device and the second angle sensor, a difference only lies in a direction: the second angle sensor is located at the far end, and the second rotation locating device is located at the near end; the third angle sensor 103 is located at the near end, and the third rotation locating device 104 is located at the far end, specifically, referring to corresponding descriptions when the guiding device shell is the above first structure, which is not repeated here.

The third angle sensor 103 detects a rotation angle of the third rotation locating device 104 and sends the rotation angle to the control device, the control device receives the rotation angle of the third rotation locating device 104 and then performs a subsequent control operation so as to make the rotation angle of the second rotation locating device be the same as the rotation angle of the third rotation locating device 104.

Thus, by means of arranging the third rotation locating device 104 and the third angle sensor 103, the rotation angle of the ablation optical fiber located in the ancillary part shell 83 may be detected, so that the control device performs the subsequent control operation so as to make the rotation angle of the ablation optical fiber 5 at the second angle sensor be the same as the rotation angle at the third angle sensor 103.

There are various structure forms of the ancillary part shell 101, which is not limited in the embodiment of the present disclosure. For example, continuing to refer to FIG. 18, the ancillary part shell 101 may include an ancillary part upper shell 1011 and an ancillary part lower shell 1012, the ancillary part lower shell 1012 includes an extending portion 10121 and a lower connection portion 10122 which are connected with each other, the ancillary part upper shell 1011 and the lower connection portion 10122 cover each other to form an accommodating cavity, and the third rotation locating device 104 and the third angle sensor 103 are mounted in the accommodating cavity.

The rotation driving device 4 is introduced below.

Referring to FIG. 4, the rotation driving device 4 includes a first driver 41, the first driver 41 is connected with the ablation optical fiber 5, and the first driver 41 drives the ablation optical fiber 5 to rotate about the major axis of the ablation optical fiber.

There are various structural forms of the first driver 41, including but not limited to a motor, a hydraulic form and a pneumatic form, which is not limited in the embodiment of the present disclosure.

There are various connection forms of the first driver 41 and the ablation optical fiber 5, for example, the rotation driving device 4 may further include a first transmission mechanism, the first driver 41 is connected with the first transmission mechanism, the first transmission mechanism is connected with the ablation optical fiber 5, and thus the first driver 41 drives the ablation optical fiber 5 through connection with the first transmission mechanism to rotate about the major axis of the ablation optical fiber.

There are various structural forms of the first transmission mechanism, including but not limited to a gear form and a belt form.

Thus, through the first driver 41, driving the ablation optical fiber 5 to rotate about the major axis of the ablation optical fiber is implemented.

Continuing to refer to FIG. 4, the rotation driving device 4 may further include a rotation device base 42, and the first driver 41 is mounted on the rotation device base 42.

During use, an ablation optical fiber of some types may be used only with the use of an adapter, for example, when the ablation optical fiber 5 is an optical fiber. FIG. 5 is a sectional view of FIG. 4. Referring to FIG. 5, the rotation driving device 4 may further include an ablation optical fiber adapter 43, and in the use state, the first driver 41 drives the ablation optical fiber adapter 43 to rotate, and the far end of the ablation optical fiber adapter 43 is connected with the ablation optical fiber 5.

The far end of the ablation optical fiber adapter 43 is connected with the ablation optical fiber 5, so that when the first driver 41 drives the ablation optical fiber adapter 43 to rotate, the ablation optical fiber adapter 43 drives the ablation optical fiber 5 to rotate along.

Continuing to refer to FIG. 5, when the ablation optical fiber 5 is the optical fiber, the above one connected with the far end of the ablation optical fiber adapter 43 is the ablation optical fiber, a transmission optical fiber is further included, the far end of the transmission optical fiber is connected with a near end of a jumper wire optical fiber connector 44, and the near end of the transmission optical fiber is connected with the laser generator. During use, the far end of the jumper wire optical fiber connector 44 is connected with the ablation optical fiber adapter 43, the jumper wire optical fiber connector 44 is securely connected with the rotation device base 42 through a jumper wire optical fiber sleeve 45, then the far end of the jumper wire optical fiber connector 44 is disconnected from the far end of the ablation optical fiber adapter 43, the ablation optical fiber adapter 43 is connected with the ablation optical fiber, at the moment, when the first driver 41 drives the ablation optical fiber adapter 43 to rotate, the ablation optical fiber adapter 43 may drive the ablation optical fiber connected therewith to rotate along, and an ablation treatment may be performed through the ablation optical fiber.

The axial movement driving device 6 is introduced below.

Referring to FIG. 11, the axial movement driving device 6 may include an axial movement driving device base 61, at least one sliding rail 62, a lead screw 63, a sliding block 64 and a second driver 65.

At least one sliding rail 62 and the lead screw 63 are arranged in parallel and is arranged through the sliding block 64, the two ends of the at least one sliding rail 62 are securely mounted on the axial movement driving device base 61, the lead screw 63 is connected to the axial movement driving device base 61, the second driver 65 drives the lead screw 63 to rotate, the second driver 65 is mounted on the axial movement driving device base 61, and the rotation driving device 4 is mounted on the sliding block 64.

During use, the second driver 65 drives the lead screw 63 to rotate, the lead screw 63 drives the sliding block 64 to move along the sliding rail, and as the rotation driving device 4 is mounted on the sliding block 64, the sliding block 64 may drive the rotation driving device 4 to move in the length direction of the ablation optical fiber 5.

There are various structural forms of the second driver 65, including but not limited to a motor, a hydraulic form and a pneumatic form, which is not limited in the embodiment of the present disclosure.

There are various connection forms of the second driver 65 and the lead crew 63, for example, the axial movement driving device 6 may further include a second transmission mechanism, the second driver 65 is connected with the second transmission mechanism, the second transmission mechanism is connected with the other end of the lead crew 63, and thus the second driver 65 drives the lead screw 63 to rotate through connection with the second transmission mechanism.

There are various structural forms of the second transmission mechanism, including but not limited to a gear form and a belt form.

For example, continuing to refer to FIG. 11, the second transmission mechanism includes a driven wheel 66, a driving wheel 67 and a belt. The second driver 65 drives the driving wheel 67 to rotate, the driving wheel 67 is connected with the driven wheel 66 through the belt, the driving wheel 67 drives the driven wheel 66 to rotate, the driven wheel 66 is connected with the other end of the lead screw 63, and the driven wheel 66 drives the lead screw 63 to rotate.

Thus, by means of arranging the sliding rail 62, the lead screw 63, the sliding block 64 and the second driver 65, the sliding block 64 may drive the rotation driving device 4 to move front and back in the length direction of the ablation optical fiber 5.

A laser thermotherapy device based on magnetic resonance guiding provided by an embodiment of the present disclosure has the same technical features as the laser thermotherapy device based on magnetic resonance guiding provided by the above embodiment, so the same technical problem may also be solved, and the same technical effects are achieved.

Those skilled in the art may clearly know that for convenient and concise description, specific workflows of the above described system and device may refer to corresponding processes in the above method embodiments, which is not repeated here.

In addition, in the description of the embodiment of the present disclosure, unless otherwise clearly specified and limited, terms “mount”, “connection” and “connected” are to be understood in a broad sense, for example, may be a secured connection, a detachable connection, or an integrated connection; may be a mechanical connection, or an electrical connection; may be a direct connection, or an indirect connection through an intermediate medium, or internal communication between two elements. Specific meanings of the above terms in the present disclosure may be understood by those ordinarily skilled in the art according to specific conditions.

It is to be noted finally that the above embodiments are merely specific implementations of the present disclosure, and are intended to describe the technical solutions of the present disclosure rather than make a limit. The protection scope of the present disclosure is not limited to this. Although the present disclosure has been described in detail with reference to the above embodiments, those ordinarily skilled in the art are to understand that any of those familiar with the art may still make modifications or easily figured changes to the technical solutions recorded in the above embodiments or make equivalent replacements to some technical features without departing from the technical scope disclosed in the present disclosure. These modifications, changes or replacements do not make the essence of the corresponding technical solutions depart from the spirit and scope of the technical solutions of the embodiments of the present disclosure and should fall within the protection scope of the present disclosure. Thus, the protection scope of the present disclosure should be subject to the protection scope of the claims.

What is claimed is:

1. A magnetic resonance guided laser ablation treatment system, comprising: an ablation optical fiber; a laser ablation apparatus, comprising a laser generator and a cooling device; a stereotactic driving system accommodating and controlling a position and/or a rotation angle of the ablation optical fiber; and a workstation, configured to: control the movement of the stereotactic driving system, and generate and display ablation information of the target region during the workflow of magnetic resonance guided laser ablation treatment system by using magnetic resonance temperature imaging technology; wherein the stereotactic driving system comprises: a guide device, a sleeve, a connector, a rotation driving device and an axial movement driving device; the near end of the sleeve is connected to the connector, and the far end of the sleeve may extend out from the far end of the guide device; and in a use state, the ablation optical fiber is arranged in the sleeve, the rotation driving device drives the ablation optical fiber to rotate and the axial movement driving device drives the ablation optical fiber along the major axis; wherein the rotation driving device comprises a first driver; and the first driver is connected with the ablation optical fiber, and the first driver drives the ablation optical fiber to rotate about the major axis of the ablation optical fiber; and the rotation driving device is in sliding connection with the axial movement driving device.

2. The magnetic resonance guided laser ablation treatment system according to claim 1, wherein the guide device comprises a hollow guiding part for an elongated structure and a clamping assembly, the far end of the clamping assembly is connected with the near end of the hollow guiding part for the elongated structure, and the clamping assembly is used for fixing the relative positions of the sleeve and the hollow guiding part for the elongated structure after the sleeve extends out of the far end of the hollow guiding part for the elongated structure.

3. The magnetic resonance guided laser ablation treatment system according to claim 1, wherein the connector comprises a sealing plug, an ablation optical fiber connector, and in sequence from near end to far end, a sealing nut, a Luer taper, a water inlet adapter, and a water outlet adapter; the ablation optical fiber connector is connected with a transmission part of the rotation driving device, the sealing plug is arranged in the Luer taper, and an internal protrusion of the sealing nut makes contact with the sealing plug; and in a use state, the sealing nut is tightened to the Luer taper, the internal protrusion of the sealing nut tightly compresses the sealing plug, and the ablation optical fiber is arranged within the inside lumen of the ablation optical fiber connector, the sealing nut, the sealing plug and the water inlet adapter to enter the sleeve.

4. The magnetic resonance guided laser ablation treatment system according to claim 3, wherein a rigid structure is arranged on the outside of at least the first portion of the ablation optical fiber, or at least the first portion of the ablation optical fiber has an external surface structure with enhanced strength, wherein the first portion comprises a portion of the ablation optical fiber which begins from the proximal end to the inside of the sealing plug and a portion of the ablation optical fiber which exceeds the far end of the sealing plug, and when the far end of the ablation optical fiber is located at a farthest end of the system, the length of the portion exceeding the far end of the sealing plug is greater than the translation movement range of the ablation optical fiber.

5. The magnetic resonance guided laser ablation treatment system according to claim 1, wherein the axial movement driving device comprises an axial movement driving device base, at least one sliding rail, a lead screw, a sliding block and a second driver; and at least one sliding rail and the lead screw are arranged in parallel and is arranged through the sliding block, the two ends of at least one sliding rail are securely mounted on the axial movement driving device base, the lead screw is connected to the axial movement driving device base, the second driver drives the lead screw to rotate, the second driver is mounted on the axial movement driving device base, and the rotation driving device is mounted on the sliding block.

6. The magnetic resonance guided laser ablation treatment system according to claim 1, wherein the ablation optical fiber may emit light laterally.

7. The magnetic resonance guided laser ablation treatment system according to claim 1, wherein the workstation may be connected in communication with the laser ablation apparatus and the stereotactic driving system, adjust parameters of the laser generator and the cooling device, control a position and a rotation angle of the ablation optical fiber, perform ablation under magnetic resonance detection, and, using temperature and ablation information from magnetic resonance images as feedback, perform control over the laser ablation apparatus and the stereotactic driving system.

8. A magnetic resonance guided laser ablation treatment system, comprising: an optical fiber cooling assembly, accommodating and cooling an ablation optical fiber; a laser ablation apparatus, comprising a laser generator and a cooling device; a stereotactic driving system, accommodating and controlling a position and/or a rotation angle of the ablation optical fiber; and a workstation, configured to: control the movement of the stereotactic driving system, and generate and display ablation information of the target region during the workflow of the magnetic resonance guided laser ablation treatment system by using magnetic resonance temperature imaging technology; wherein the stereotactic driving system comprises: a guiding device, comprising a cooling sleeve guide part and a guiding device shell; at least two sensor assemblies, each comprising an angle sensor; a rotation driving device and an axial movement driving device, the rotation driving device drives the ablation optical fiber to rotate and the axial movement driving device drives the ablation optical fiber along the major axis; and a controller, being connected in communication with the sensor assemblies and the rotation driving device, receiving output angle information from the sensor assemblies, controlling the movement of the rotation driving device and further receiving control information; wherein in a use state, the far end of the ablation optical fiber is arranged within the inside lumen of the optical fiber cooling assembly, the angle sensors are securely connected to a device or a structure which does not rotate together with the ablation optical fiber; wherein the stereotactic driving system further comprises a sleeve, the sleeve ensures that the length between the first sensor assembly and the second sensor assembly remains secure, and allows the ablation optical fiber to rotate about its major axis and move along the major axis in the sleeve.

9. The magnetic resonance guided laser ablation treatment system according to claim 8, wherein the optical fiber cooling assembly comprises a cooling liquid conveying pipe, a cooling sleeve, a water circulation adapter assembly and a sealing plug.

10. The magnetic resonance guided laser ablation treatment system according to claim 8, wherein each sensor assembly further comprises a rotation locating device, so that the ablation optical fiber may move along the major axis while the rotation angle is measured, in a use state, the rotation locating device clamps the ablation optical fiber according to a preset pressure, the ablation optical fiber drives the rotation locating device to rotate, and the angle sensors detect the rotation angle of the rotation locating device and send the rotation angle to the controller.

11. The magnetic resonance guided laser ablation treatment system according to claim 8, wherein the stereotactic driving system further comprises an axial movement driving device, the rotation driving device may move relative to the axial movement driving device, the controller sends control information to the axial movement driving device, and thus the ablation optical fiber moves along the major axis.

12. The magnetic resonance guided laser ablation treatment system according to claim 11, wherein the axial movement driving device is connected with the rotation driving device.

13. The magnetic resonance guided laser ablation treatment system according to claim 8, wherein in the stereotactic driving system, the guiding device shell comprises a bone screw cap, a guiding device shell body and a guiding device shell rear cover; the near end of the cooling sleeve guide part is in threaded connection with the far end of the bone screw cap, a near end of the bone screw cap is connected with the far end of the guiding device shell body, the guiding device shell rear cover is connected with a near end of the guiding device shell body, the guiding device shell rear cover is connected with the far end of the sleeve, and the optical fiber cooling assembly is arranged in the guiding device shell body; and in a use state, the ablation optical fiber arranged through the guiding device shell rear cover, the guiding device shell body, the bone screw cap and the cooling sleeve guide part.

14. The magnetic resonance guided laser ablation treatment system according to claim 13, wherein in the stereotactic driving system, the guiding device shell body comprises a guiding device shell body fixed portion and a guiding device shell body sliding portion, the near end of the bone screw cap is connected with the far end of the guiding device shell body fixed portion, a near end of the guiding device shell body fixed portion is connected with the far end of the guiding device shell body sliding portion, and the guiding device shell rear cover is connected with the near end of the guiding device shell body sliding portion.

15. The magnetic resonance guided laser ablation treatment system according to claim 8, wherein the stereotactic driving system comprises: a guide device, a sleeve, an ancillary part, a rotation driving device and an axial movement driving device; and the guiding device comprises the cooling sleeve guide part and the guiding device shell, the guiding device shell comprises a bone screw cap, a guiding device shell body and a guiding device shell rear cover, the guiding device shell body comprises a guiding device shell body fixed portion and a guiding device shell body sliding portion, the near end of the bone screw cap is connected with the far end of the guiding device shell body fixed portion, the near end of the guiding device shell body fixed portion is connected with the far end of the guiding device shell body sliding portion, the guiding device rear cover covers the near end of the guiding device shell body sliding portion, a graduated scale is arranged on the guiding device shell body fixed portion and/or the guiding device shell body sliding portion, the guiding device shell body fixed portion and the guiding device shell body sliding portion may move relative to each other, the graduated scale displays a distance of a relative movement, the first sensor assembly is arranged in the guiding device, and the angle sensor of the first sensor assembly is connected with the guiding device shell body; the second sensor assembly is arranged in the ancillary part, the angle sensor of the second sensor assembly is connected with a shell of the ancillary part, the ancillary part is connected with the axial movement driving device, and thus the relative positions of the ancillary part and the axial movement driving device are unchanged; the far end of the sleeve is connected with the guiding device rear cover, the near end of the sleeve is connected with the ancillary part, and thus a length between the guiding device rear cover and the ancillary part is unchanged; the rotation driving device is in sliding connection with the axial movement driving device; and in a use state, the optical fiber cooling assembly is arranged within the guiding device shell body.

* * * * *